United States Patent [19]
Gilmore et al.

[11] Patent Number: 5,931,160
[45] Date of Patent: Aug. 3, 1999

[54] VENTILATOR CONTROL SYSTEM AND METHOD

[75] Inventors: Don Gilmore, Brighton; Douglas Johnston, Winchester, both of Mass.; Gary Schroeder, North Londonderry, N.H.

[73] Assignee: Cardiopulmonary Corporation, Milford, Conn.

[21] Appl. No.: 08/569,919

[22] Filed: Dec. 8, 1995

[51] Int. Cl.$^6$ .................................................. A61M 16/00
[52] U.S. Cl. ............................... 128/204.21; 128/204.18; 128/204.23; 128/205.23
[58] Field of Search .................... 128/204.18, 204.21, 128/204.23, 205.23, 697, 699, 710

[56] References Cited

U.S. PATENT DOCUMENTS

| | | |
|---|---|---|
| 3,212,496 | 10/1965 | Preston . |
| 3,741,208 | 6/1973 | Jonsson et al. ..................... 128/204.21 |
| 3,835,845 | 9/1974 | Maher . |
| 3,923,055 | 12/1975 | Hammacher ....................... 128/204.21 |
| 3,961,627 | 6/1976 | Ernst et al. ........................ 128/204.21 |
| 3,972,327 | 8/1976 | Ernst et al. ........................ 128/204.21 |
| 4,016,871 | 4/1977 | Schiff . |
| 4,036,221 | 7/1977 | Hillsman et al. . |
| 4,163,450 | 8/1979 | Kirk et al. ......................... 128/204.21 |
| 4,204,524 | 5/1980 | Martin et al. ............................ 600/17 |
| 4,256,150 | 3/1981 | Levy et al. ......................... 128/204.21 |

(List continued on next page.)

FOREIGN PATENT DOCUMENTS

| | | |
|---|---|---|
| 0 274 996 | 12/1987 | European Pat. Off. ........ A61M 16/00 |
| 0 342 443 | 5/1989 | European Pat. Off. ........ A61M 16/00 |
| 2729084 | 12/1995 | France . |
| 2348582 | 9/1973 | Germany . |
| 8/801322 | 5/1988 | Netherlands . |
| 2162430 | 8/1984 | United Kingdom .......... A61M 16/00 |

OTHER PUBLICATIONS

Jim Hitchin, "Computerized Pulmonary Diagnostics for Infants and Children" *Biomedical Business International* Section 7: 1–3/24 (May 23, 1990).
Puritan Bennett "Puritan Bennett 7200 Series Ventilator, Optics, and Accessories — Operation'Manual — Part No. 22300A" *Marketing Communications Department — Puritan–Bennett Corporation* 1–6/9 (Sep. 1990).
Bear Medical Systems, Inc. "Bear 5 Medical Ventilator Instruction Manual" *Bear Medical Systems, Inc.* (1985).
Adult Star Ventilator "Adult Star Ventilator Operating Instructions" *Adult Star Ventilator.*
Hamilton Medical "Veolar Operator's Manual" *Hamilton Medical* (Jul. 1988).
Siemens "Servo Ventilator 300 Service Manual — Preliminary" *Siemens* (1991).
Siemens "Servo Ventilator 900C Operating Manual" *Siemens.*

*Primary Examiner*—John G. Weiss
*Assistant Examiner*—V. Srivastava
*Attorney, Agent, or Firm*—Testa, Hurwitz & Thibeault, LLP

[57] ABSTRACT

A ventilator control system controls a ventilator pneumatic system in a medical ventilator. The ventilator control system includes a user interface, a memory and a processor. The user interface receives input values from a user for setting one or more breath parameters within a set of breath parameters. The user interface can include a display for displaying the status of the patient's pulmonary system and the set of breath parameters. The memory stores the set of breath parameters after the user has set one or more breath parameters to desired input values. The processor simultaneously adjusts a plurality of controls within a ventilator pneumatic system in response to the set of breath parameters. The user can change or implement new phases, breaths, modes or therapies in seconds such that the therapy delivered to the patient is essentially uninterrupted. Also, a simulator may be provided for predicting the status of the patient's pulmonary system prior to adjusting the plurality of controls. The predicted status may be displayed adjacent the current status on the display.

40 Claims, 12 Drawing Sheets

U.S. PATENT DOCUMENTS

| | | | |
|---|---|---|---|
| 4,323,064 | 4/1982 | Hoenig et al. | 128/204.21 |
| 4,340,044 | 7/1982 | Levy et al. | 128/204.21 |
| 4,413,632 | 11/1983 | Schlessinger et al. | 128/716 |
| 4,424,806 | 1/1984 | Newman et al. | 128/28 |
| 4,444,201 | 4/1984 | Itoh | 128/204.23 |
| 4,448,192 | 5/1984 | Stawitcke et al. | 128/204.26 |
| 4,546,770 | 10/1985 | Schlessinger et al. | 128/630 |
| 4,838,257 | 6/1989 | Hatch . | |
| 4,917,080 | 4/1990 | Bayerlein | 128/204.23 |
| 4,928,674 | 5/1990 | Halperin et al. | 128/204.26 |
| 4,984,158 | 1/1991 | Hillsman | 128/200.14 |
| 4,986,268 | 1/1991 | Tehrani | 128/204.22 |
| 4,990,894 | 2/1991 | Loescher et al. | 128/204.21 |
| 5,020,516 | 6/1991 | Biondi et al. | 128/30.2 |
| 5,072,737 | 12/1991 | Goulding | 128/718 |
| 5,097,424 | 3/1992 | Ginevri et al. | 364/510 |
| 5,107,831 | 4/1992 | Halpern et al. | 128/30.2 |
| 5,129,390 | 7/1992 | Chopin et al. | 128/204.21 |
| 5,183,038 | 2/1993 | Hoffman et al. | 128/204.21 |
| 5,188,098 | 2/1993 | Hoffman et al. | 128/204.23 |
| 5,303,698 | 4/1994 | Tobia et al. | 128/204.21 |
| 5,309,919 | 5/1994 | Snell et al. | 600/510 |
| 5,331,995 | 7/1994 | Westfall et al. | 137/8 |
| 5,402,796 | 4/1995 | Packer et al. | 128/204.22 |
| 5,429,123 | 7/1995 | Shaffer et al. | 128/204.23 |
| 5,549,106 | 8/1996 | Gruenke et al. | 128/204.21 |

VENTILATOR CONTROL SYSTEM AND METHOD

FIELD OF THE INVENTION

The invention relates generally to the field of respiratory assist devices such as ventilators. In particular, the invention relates to a ventilator control system and method for controlling a ventilator pneumatic system.

BACKGROUND OF THE INVENTION

A medical ventilator delivers gas to a patient's respiratory tract and is often required when the patient is unable to maintain adequate ventilation. Mechanical ventilation is the single most important therapeutic modality in the care of critically ill patients. Known ventilators typically include a pneumatic system that delivers and extracts gas pressure, flow and volume characteristics to the patient and a control system (typically consisting of knobs, dials and switches) that provides the interface to the treating clinician. Optimal support of the patient's breathing requires adjustment by the clinician of the pressure, flow, and volume of the delivered gas as the condition of the patient changes. Such adjustments, though highly desirable, are difficult to implement with known ventilators because the control system demands continuous attention and interaction from the clinician.

Ventilatory modes are methodologies for controlling the pressure, flow and volume characteristics of the breaths to be delivered, and are preset in known ventilators during the manufacturing process. Various ventilatory modes have evolved to support breathing for patients with different pathologies at different stages of the course of treatment. Examples of such modes include intermittent mandatory ventilation (IMV), assist-control ventilation (A/C), pressure support ventilation (PS) and continuous positive airway pressure (CPAP).

One limitation of known ventilators is that selection of a ventilatory mode imparts specific and often inconsistent instructions to the ventilator controls. Another problem is that modes having the same or similar names are often preset differently on different ventilators. This characteristic of known ventilators has led to unsuccessful attempts to enforce standard definitions for ventilatory modes, and has resulted in the requirement of extensive training of clinical personnel.

Another limitation of known ventilators is the difficulty and uncertainty when changing ventilatory modes. A large number of control and alarm settings are changed by the clinician to implement a new mode. While the settings are being changed, a time period of up to several minutes, the therapy delivered to the patient is uncontrolled. Typically, the clinician disconnects the patient from the ventilator and provides manual support during the transition to the new mode. In addition, clinicians are often uncertain about the breathing pattern the new mode will produce when applied to a particular patient. This discourages clinicians from trying new modes which might better accommodate the patient, and encourages prolonged use of existing modes to control the patient's breathing via the ventilator, thereby inhibiting the patient's respiratory drive. The patient spends more time than necessary on ventilatory support, leading to slower recovery and increased risk of complications.

Yet another limitation of the known ventilators is that new features, in particular new types of breaths and new ventilatory modes, can only be provided by physically changing the memory device containing the software programs. A clinician with a new type of therapy must navigate a lengthy and circuitous development path to implement the therapy on a patient. First, the clinician must explain the therapy to the representatives of a ventilator manufacturer, convince them that the therapy is commercially viable, and direct the manufacturer through several design/development cycles over a period of many months. If the therapy is shown to be beneficial, an additional lengthy delay occurs for manufacturing startup and regulatory approval. This frustrating pathway significantly inhibits the development of new types of therapy in ventilation.

A further limitation of the control interfaces of known ventilators is the provision for control of only a single mode of ventilation. The needs of patients are continuously changing, and a principal focus of ventilatory therapy is to "wean" the patient from full ventilatory support to self-supported breathing. During this transition, which can take days to weeks, the ventilator must accommodate and encourage efforts by the patient to breathe and "synchronize" its efforts with patient-induced breathing. Delivery of an optimal breathing pattern requires delivery of respiratory gas to the patient at the appropriate time and rate, and removal of the respiratory gas at the appropriate time and rate. Known ventilators require frequent encounters between the clinician and the patient to adjust the breathing pattern. Because such encounters tend to be widely spaced, patients spend long periods between such encounters "fighting" the ventilator as it tries to deliver breaths which do not match their needs.

Another limitation of the user interface on known ventilators is the separation of the control settings, the alarm settings and the patient data into different areas of focus for the clinician. The clinician is required to mentally integrate the control settings, alarm settings and patient data to determine whether the current therapy is appropriate. The ventilator interface is interposed between the clinician and the patient, obscuring both the therapy and the condition of the patient with unnecessary complexity.

For many of the reasons described above, known ventilators require a high level of skill and interaction from clinicians. Many clinicians lack the required exposure and training to command the ventilator to deliver the appropriate therapy for the wide variety of patient conditions.

It is therefore a principal object of the invention to provide a ventilator control system which is connected to a ventilator pneumatic system for controlling the selection of ventilatory modes to maintain desired pressure, flow and volume characteristics of the breaths delivered to a patient. It is another object of the invention to provide a ventilator control system that enables a clinician to prescribe a series of ventilator breaths, modes or therapies to accommodate changes in a patient's condition. It is another object of the invention to provide a ventilator control system that enables a clinician to access stored historical patient data for clinician training or patient therapy. It is another object of the invention to provide a ventilator control system that enables a clinician to create new ventilator breaths, modes or therapies on demand. It is another object of the invention to provide a ventilator control system that simulates the effect of a new ventilator mode on a patient, before actually implementing the new mode on the patient.

SUMMARY OF THE INVENTION

The term "ventilator control setting structure" is defined as a collection of information sufficient to control one parameter of ventilation including one or more of: high alarm level, high alarm active, control level, control level active, low alarm level, low alarm active, range level, range level active, and a range target control structure. The range target control structure defines how and why the parameter is to be adjusted automatically within the specified range. The term "cycle control structure" is defined as a collection of waveform samples and a ventilator control setting Structure for each parameter. The term "phase control structure" is defined as a collection of phase switching rules that defines how the ventilator control settings are to be utilized and a ventilator control setting for each controllable parameter that exists in the ventilator. Each phase has one or more triggers that are tested every cycle (4 Msecs per cycle) to decide which ventilator control setting to use. The term "breath control structure" is defined as a collection of phase switching rules that defines how and when one ventilatory breath phase is to switch to another ventilatory breath phase and a phase control structure for each phase of breath defined by the specified breath. Breath phases break up a ventilatory breath into as many phases as desired in order to control inspiration, pause, expiration assist and positive end-expiratory pressure (PEEP) with any desired level of control for the specified breath. Each breath has one or more triggers that are tested every cycle (4 Msecs per cycle) to decide whether or not to jump to the beginning of a new phase control structure. The term "mode control structure" is defined as a collection of breath switching rules that defines how and when one ventilatory breath is to switch to another ventilatory breath and a breath control structure for each type of breath defined by the specified mode of ventilation. Each mode has one or more triggers that are tested every cycle (4 Msecs per cycle) to decide whether or not to jump to the beginning of a new breath control structure. The term "therapy control structure" is defined as a collection of mode switching rules that defines how and when one mode of ventilation is to switch to another mode of ventilation and one mode control structure for each ventilation mode defined by the specified therapy. Also, the term "breath parameter" is defined as at least one of a control setting and an alarm setting.

The present invention features a ventilator control system for controlling a ventilator pneumatic system. The ventilator control system includes a user interface, a memory and a processor. The user interface receives input values from a user for setting one or more breath parameters within a set of breath parameters. The user interface can include a display for displaying software-generated images representing status of the patient's pulmonary system and the set of breath parameters. Also, a touch-sensitive screen may be disposed over the display for manipulating one or more breath parameters.

The memory is electrically coupled to the user interface for storing the set of breath parameters after the user has set one or more breath parameters to the desired input values. The processor simultaneously adjusts a plurality of controls within a ventilator pneumatic system in response to the set of breath parameters. More specifically, the processor may comprise a display controller for creating a therapy control structure, a mode control structure, a breath control structure or a phase control structure from the set of breath parameters stored in the memory and an embedded controller for simultaneously changing the plurality of controls within the ventilator pneumatic system in response to the structure. The ventilator control system enables the user to change or implement a new therapy, mode, breath or phase in seconds so that the therapy delivered to the patient is essentially uninterrupted, and the new therapy is synchronized with the next inspiration.

The invention also features a method for controlling a ventilator pneumatic system. The method includes the step of receiving input values provided by a user for setting one or more breath parameters within a set of breath parameters, and the step of simultaneously adjusting a plurality of controls within the ventilator pneumatic system in response to the set of breath parameters. The method may also include the step of creating a therapy control structure, a mode control structure, a breath control structure or a phase control structure from the set of breath parameters, and the step of simultaneously changing the plurality of controls within the ventilator pneumatic system in response to the structure. Further, the method may include the step of displaying software-generated images representing status of the patient's pulmonary system and the set of breath parameters on a display.

The invention also features a ventilator control system capable of simulating the status of a patient connected to a ventilator pneumatic system. The system includes a user interface for receiving input values to define one or more breath parameters within a set of breath parameters. A simulator is electrically connected to the user interface for receiving the set of breath parameters. The simulator predicts the status of the patient's pulmonary system by simulating (i) an adjustment to the controls within the ventilator pneumatic system in response to the set of breath parameters and (ii) a response of the patient's pulmonary system to the adjustment to the controls within the ventilator pneumatic system. The ventilator control system also includes a display on which software-generated images representing the predicted status of the patient's pulmonary system and the set of breath parameters are provided. A touch-sensitive screen may be disposed over the display for manipulating one or more breath parameters.

The invention also features a method for simulating status of the pulmonary system of a patient connected to a ventilator pneumatic system. The method includes the steps of (i) setting one or more breath parameters within a set of breath parameters, (ii) predicting the status of the patient's pulmonary system by simulating an adjustment to the controls within the ventilator pneumatic system in response to the set of breath parameters and a response of the patient's pulmonary system to the adjustment to the controls within the ventilator pneumatic system, and (iii) displaying software-generated images representing the predicted status of the patient's pulmonary system and the set of breath parameters.

The invention also features a method for generating a breath control structure to control a ventilator pneumatic system. The method includes the step of providing a set of breath parameters. Each breath parameter within the set of breath parameters includes at least one of a control setting or alarm setting. The method also includes the step of setting control settings and alarm settings for one or more breath parameters within the set of breath parameters. Further, the method includes the step of creating a breath control structure from the set of breath parameters, wherein a plurality of controls within a ventilator pneumatic system are adjusted in response to the breath control structure.

The invention also features a method for generating a mode control structure to control a ventilator pneumatic system. The method includes the step of providing a first set of breath parameters. Each breath parameter within the first set of breath parameters includes at least one of a control or alarm setting. The method also includes the steps of providing user selected input values to define at least one of the control or alarm setting for one or more breath parameters within the first set of breath parameters, and creating a first breath control structure from the first set of breath parameters. Further, the method includes repeating the three previously described steps for a second set of breath parameters to create a second breath control structure. The method also includes the step of combining the first and second breath control structures to form a mode control structure, wherein a plurality of controls within a ventilator pneumatic system are adjusted in response to the mode control structure.

The invention also features a method for providing a therapy to a patient connected to a ventilator pneumatic system. The method includes the step of providing a first mode control structure, including a plurality of breath control structures, and a second mode control structure, including a plurality of breath control structures. The method also includes the steps of controlling a plurality of controls within a ventilator pneumatic system using the first mode control structure, and measuring one or more therapy parameters. Further, the method includes the step of adjusting the plurality of controls within a ventilator pneumatic system using the second mode control structure when one or more parameters exceed predetermined trigger values.

The invention also features a ventilator control system for controlling a ventilator pneumatic system using historical patient data stored in a database. The ventilator control system includes a database which stores a plurality of patient protocols, each patient protocol comprising a set of breath parameters and patient data. A user interface is electrically coupled to the database for selecting a patient protocol. A processor is electrically coupled to the user interface for receiving the selected patient protocol. The processor simultaneously adjusts controls within the ventilator pneumatic system using the selected patient protocol. The ventilator control system may include a display on which software-generated images representing status of the patient's pulmonary system and the set of breath parameters are displayed. The user interface may comprise a touch-sensitive screen disposed over the display for manipulating one or more breath parameters.

The invention also features a method for controlling a ventilator pneumatic system using historical patient data stored in a database. The method includes the step of providing a database including a plurality of patient protocols. Each patient protocol comprises a set of breath parameters and patient data. The method also includes the steps of accessing the database to select a patient protocol, and loading a processor with the selected patient protocol. Further, the method includes the step of adjusting a plurality of controls within the ventilator pneumatic system using the selected patient protocol.

The method may also comprise the step of predicting the status of the patient's pulmonary system prior to adjusting the controls of the ventilator pneumatic system by simulating adjusting the controls in response to the set of breath parameters, and simulating a response of the patient's pulmonary system to the adjustment to the controls. Further, the method may comprise the step of displaying software-generated images representing the predicted status of the patient's pulmonary system and the set of breath parameters on a display. The method may also comprise the step of adjusting the plurality of controls within the ventilator pneumatic system based on the predicted status of the patient's pulmonary system and the set of breath parameters displayed on the display.

The invention also features a method for providing an assisted phase of a breath to a patient connected to a ventilator pneumatic system. The method includes the step of monitoring an accumulated volume of gas inhaled by the patient resulting from the particular spontaneous respiratory muscle activity. More specifically, the monitoring step further comprises measuring a flow of gas inhaled by the patient resulting from the patient's spontaneous respiratory muscle activity, and integrating the flow to provide the measured accumulated volume. The method also includes the steps of comparing the measured accumulated volume to a trigger volume, and adjusting the plurality of controls within the ventilator pneumatic system when the measured accumulated volume exceeds the trigger volume to provide an assisted phase of a breath. The method also includes the steps of adjusting the trigger volume dynamically according to measured patient flow and pressure signals indicating the phase of respiratory cycle.

The invention also features a method of compensating for gas flow resistance into and out of the lungs of a patient connected to a ventilator pneumatic system. The method includes the steps of measuring the gas flow resistance into and out of the lungs of a patient, or setting a resistance parameter to a selected value, and adjusting one or more controls of the ventilator pneumatic system to compensate for the measured or set resistance to flow. Further, the method includes adjusting one or more controls of the ventilator pneumatic system to compensate for the measured or set resistance to flow during any one or more of the inspiration, exhalation or passive phases of a breath. Further, the method allows compensation for a different measured or set resistance during one or more phases of a breath.

The invention also features a method for controlling a ventilator pneumatic system using an integrated, multi-function, software-generated graphic. The method includes the step of providing a set of breath parameters for controlling the ventilator pneumatic system, the set of breath parameters including at least one range parameter. The method also includes the step of displaying a multi-function, software-generated graphic that includes an integrated, software-generated image representing a controllable high alarm level, a controllable low alarm level, a controllable nominal operating value, a controllable operating range for the range parameter, and a controllable target value for a measured characteristic of the patient's pulmonary system. Further, the method includes the steps of setting the high alarm level to a maximum allowable value for the range parameter, setting the low alarm level a minimum allowable value for the range parameter, setting the nominal operating value for the range parameter, and setting the operating range to a range of allowable operating values relative to the nominal operating value for the range parameter. Further, the method includes the step of automatically restricting the setting of nominal operation value, and the range of allowable operating values, within the high and low alarm levels. The method also includes the steps of specifying the target value, adjusting a plurality of controls within a ventilator pneumatic system in response the set of breath parameters, and adjusting the operating value of the range parameter within the operating range. Further, the method includes the step of further adjusting the controls within the ventilator pneumatic system in response to changes in the operating value of the range parameter to achieve the target value.

The invention also features a method of manipulating a breath parameter represented as a software-generated image displayed on a touch-sensitive display. The method includes the steps of dynamically defining an touch zone on the touch-sensitive display, and forming a software-generated image of a breath parameter within a subsection of the touch zone. The method also includes the steps of receiving a touch signal when a user touches any location within the touch zone, and manipulating the image of the breath parameter in response to the touch signal.

The invention also features a method of displaying historical status of the pulmonary system of a patient connected to a ventilator pneumatic system. The method includes the steps of defining a measurement period of one minute, and providing a plurality of breath parameters having user defined target values and actual values, the breath parameters including minute volume, inspiration phase, exhalation phase, inspiration/exhalation ratio, breathing rate, spontaneous minute volume, inhale tidal volume, exhale tidal volume, leakage. The method also includes the steps of measuring the actual values during the measurement period, and generating an integrated graphic for displaying the input values and actual values of the plurality of breath parameters on a display. The generating step further comprises the steps of (i) representing target minute volume as a circle having an area corresponding to the user defined target value of the minute volume, (ii) representing actual minute volume as a semi-transparent circle disposed over the target minute volume circle and having an area corresponding to the actual value, (iii) representing target inspiration and exhalation phases as interspersed wedges within the target minute volume circle, wherein a target inspiration phase and a target exhalation phase form a target breath, and (iv) representing measured inspiration and exhalation phases as interspersed semi-transparent wedges disposed over the target inspiration and exhalation phase wedges and having an area corresponding to the actual value, wherein a measured inspiration phase and a measured exhalation phase form a measured breath. The method also includes the step of updating the input values and measured values included in the graphic once per breath. The method further comprises the steps of (v) representing the patient triggered spontaneous breaths in one color and (vi) representing the triggered mandatory breaths in a second color for displaying the ratio of mandatory to spontaneous breaths graphically as a ratio of areas.

BRIEF DESCRIPTION OF THE DRAWINGS

The foregoing and other objects, features and advantages of the invention will become apparent from the following more particular description of preferred embodiments of the invention, as illustrated in the accompanying drawings.

DETAILED DESCRIPTION

1. Ventilator Control System—The invention features a ventilator control system for controlling a ventilator pneumatic system in a medical ventilator. The ventilator control system provides a clinician with complete control of a patient's airway flow and pressure throughout the respiratory cycle, and thereby enables the clinician to determine the optimal therapy for the patient.

Figure 1:
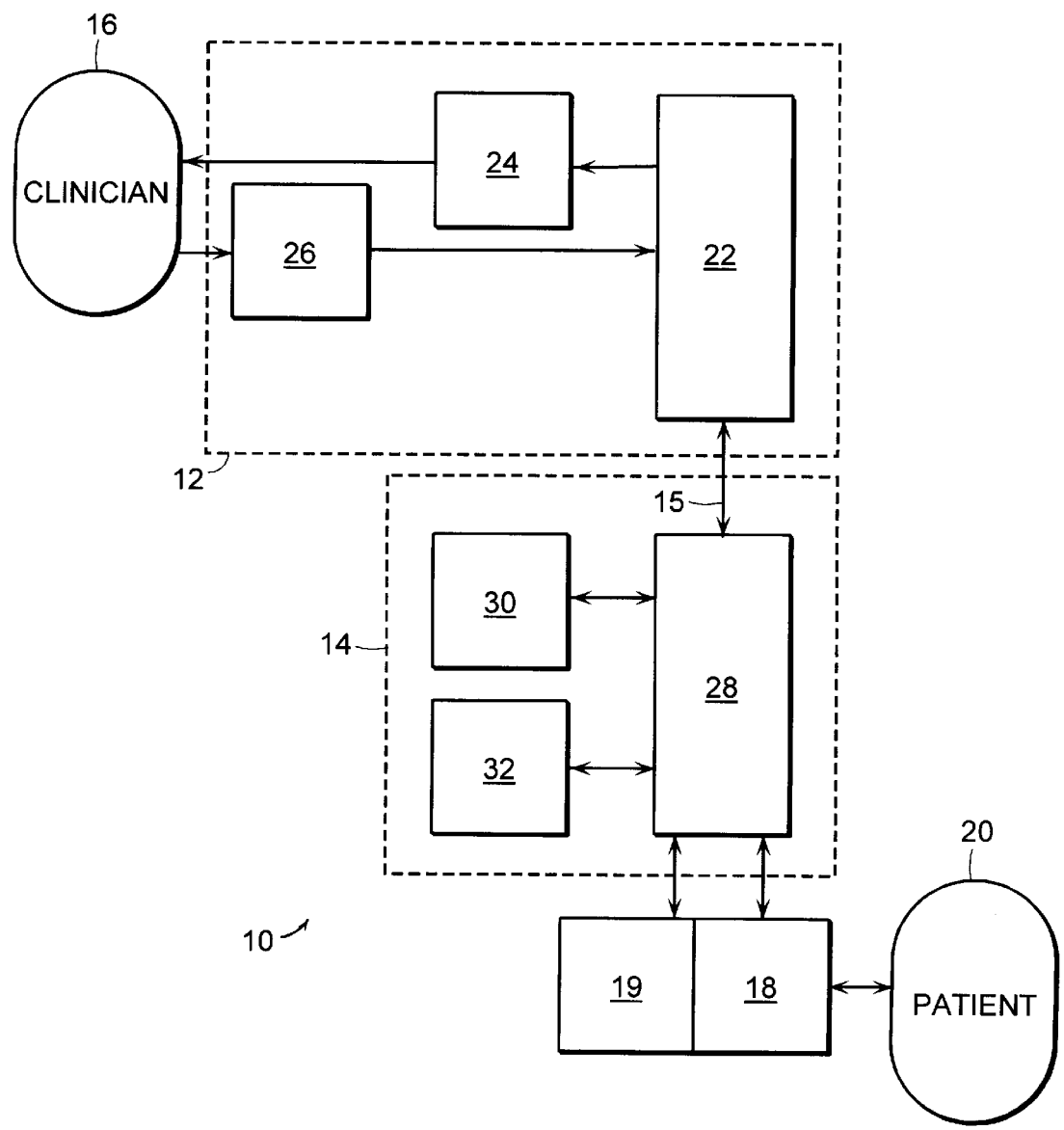
FIG. 1 is a block diagram of a ventilator including a ventilator control system illustrating the principles of the invention.

FIG. 1 is a block diagram of a ventilator including a ventilator control system 10 incorporating the features of the invention. The ventilator control system 10 includes a display controller 12 and an embedded controller 14. The display controller 12 provides an interface to the clinician 16, and the embedded controller 14 provides an interface to a ventilator pneumatic system 18 connected to a patient 20. The display controller 12 and the embedded controller 14 each include memory (not shown) and are electrically coupled via a shared memory interface 15.

The display controller 12 includes a processor 22, a display 24 and a touchscreen 26 disposed over the display. The processor 22 collects inputs from the clinician 16, validates the inputs, creates a therapy control structure from the inputs and sends the resulting structure to the embedded controller 14. The therapy control structure is a hierarchical arrangement of similar data structures which includes one or more mode control structures, one or more breath control structures, one or more phase control structures and one or more cycle control structures. The CRT display 24 maintains and displays the patient's history in a graphical format which highlights the patient's status. More specifically, the display 24 provides a visual indication of the current breath control parameters, alarm and fault conditions, and the current status of the patient's pulmonary system, including gas pressure, flow and volume. The resistive touchscreen 26 covers the surface of the CRT display 24 and provides a straightforward, highly flexible means to change control settings.

While the display controller 12 provides interpretation and decision support information on the CRT display 24, the ventilator does not change any breath control parameters unless directed by the clinician. Nevertheless, the display controller 12 provides a flexible user interface with multiple interactive levels, from simple text menus of controls for inexperienced users, to complete visual feedback for clinicians who understand the patient models and can intervene more aggressively and effectively.

The embedded controller 14 performs real time control of the pneumatic system 18. The embedded controller 14 includes a system board 28, a real time processor 30 and a D/A and A/D conversion module 32. The processor 30 manages sensor data collection from the sensor monitoring system 19, processes measured data, performs alarm/fault detection, and provides control data to the pneumatic system 18. The pneumatic system 18 controls gas flows and pressures in the patient's airway using a patient circuit. An electro-mechanical fresh gas flow control and measurement system provides a metered blend of oxygen and air via a heated, humidified gas delivery system. A high speed pneumatically driven, electronically controlled proportional valve and dual venturi system provides bi-directional flow and pressure control. Pressure and flow sensors provide feedback control of the desired breathing pattern and verify operation within safe limits. The pneumatic and electronic systems and patient circuit are described in extensive detail in commonly assigned U.S. patent application, Ser. No. 08/352,658, now U.S. Pat. No. 5,664,563, issued Sept. 9, 1997, is incorporated herein by reference.

The safe performance of the ventilator 10 is enhanced by the redundancy of the two independent display controller and embedded controller processors, which continually check each other's performance via the shared memory interface 15. The embedded controller 14 communicates its status, and that of the patient, to the display controller 12. The embedded controller maintains a non-volatile record of the therapy control structure and continues to operate at the last known good settings if communication becomes lost. The two systems which comprise the ventilator gives both audible and visual messages when an alarm condition exists, and maintain an alarm history. They provide alarms and mandatory patient support upon detection of apnea (i.e., the detected absence of breathing). During operation, both systems perform background tests to detect system faults. The ventilator provides a series of reduced operation modes to provide life support if system capability is compromised.

Figure 2:
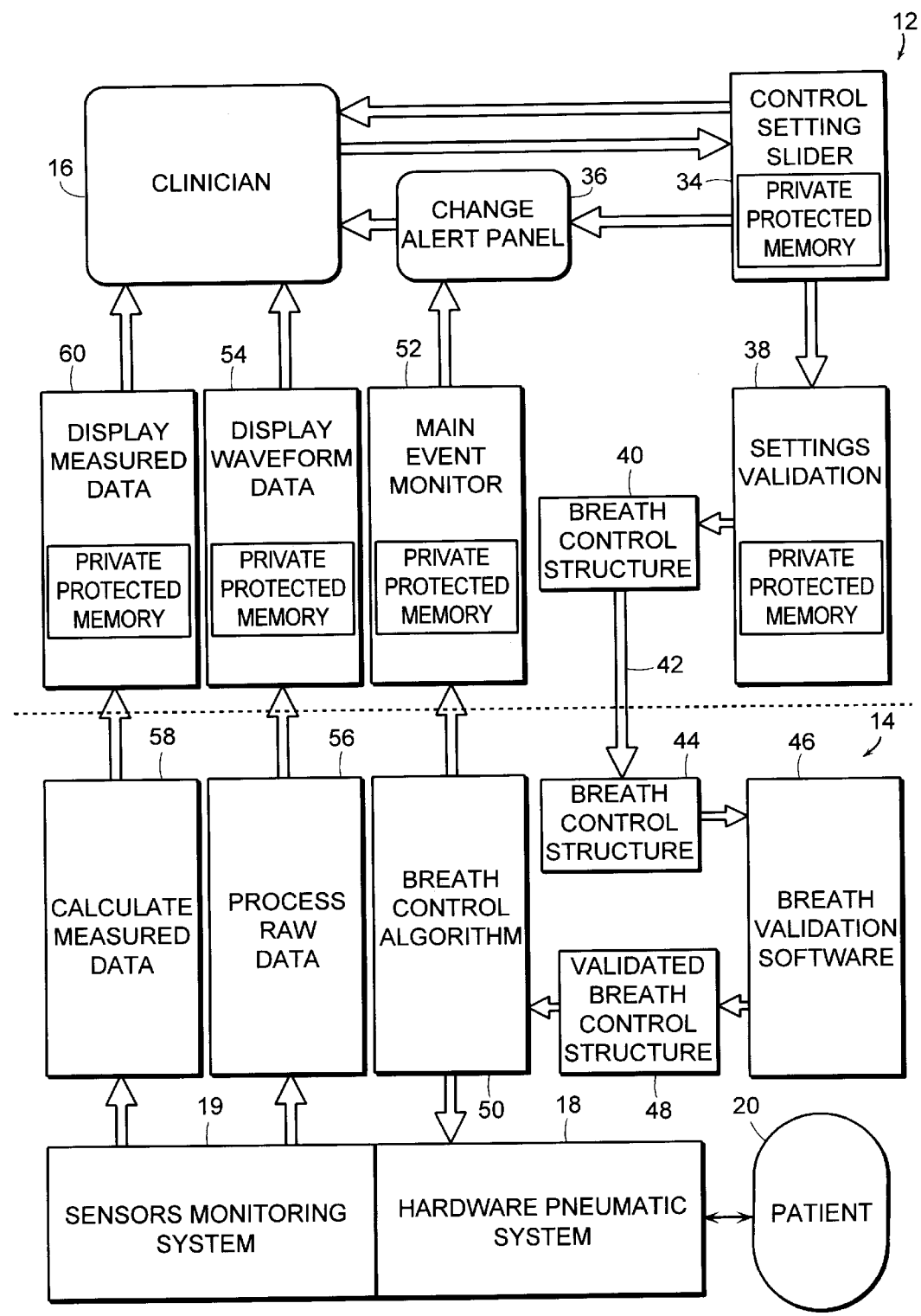
FIG. 2 is a functional block diagram illustrating the functionality of a display controller and an embedded controller within a ventilator control system.

FIG. 2 is a detailed functional block diagram of the ventilator control system 10. As shown, the clinician manipulates a control setting slider 34 to change or set one or more breath parameters. A change alert panel 36 on the display 24 informs the clinician of the process, from input to implementation, to assure him that his inputs are being processed properly. As noted previously, a change to one or more breath parameters will lead to changes in one or more data structures of the therapy control structure hierarchy. It is noted that FIG. 2 provides an example of a breath parameter change which results in a change at the level of the breath control structure. The validation process includes the processor 22 validating the clinician's inputs (at 38) and creating a breath control structure which is stored in memory (at 40). The processor transmits the breath control structure to the real time processor (at 42) and informs the clinician of successful transmission via the change alert panel. The real time processor 30 initially stores the breath control structure in another memory 44. Ultimately, the real time processor re-validates the settings within the breath control structure (at 46). The processor implements the validated breath control structure 48 in a breath control algorithm (at 50) and provides signals to the pneumatic system 18 for simultaneously changing one or more control settings at the appropriate time. This process enables the user to change or implement a new therapy so that the therapy delivered to the patient is essentially uninterrupted, and the new therapy is sychronized with the next inspiration. If, however, any step in the process is not completed, the clinician is alerted via the panel 36 to the cause of the error and the process is terminated.

The ventilator control system provides two independent feedback paths to assure the clinician that his setting change has been properly implemented. First, the embedded controller calculates a series of breath monitoring values and sends them to the display controller, where the values are displayed contiguous to the desired setting controls (at 60). The breath monitoring values can be, for example, set breath rate, measured breath rate, set tidal volume, measured inhaled volume, and measured exhaled volume. The display controller also performs a series of measurements (e.g., peak airway pressure, peak airway flow, and PEEP) from the waveform data (at 58) and displays the measurements numerically and graphically (at 60). Second, the display controller displays the continuous waveforms on the CRT display (at 54). The waveforms are derived from raw data returned from the embedded controller and passed directly to the display (at 56).

One feature of the ventilator control system 10 is that it can be configured to provide an assisted phase of a breath to the patient 20. As noted previously, the accumulated volume of gas inhaled by the patient as a result of his spontaneous respiratory muscle activity can be monitored. To accomplish this, the sensor monitoring system 19 measures the flow of gas inhaled by the patient 20 at the beginning of the inspiration phase of the breath and integrates the flow to provide the measured volume. The embedded controller 14 compares the measured volume to a trigger volume set by the clinician 16, and adjusting the plurality of controls within the ventilator pneumatic system when the measured accumulated volume exceeds the trigger volume to provide an assisted phase of a breath. The embedded controller 14 also may adjust the trigger volume dynamically according to measured patient flow and pressure signals indicating the phase of the respiratory cycle. In particular, the embedded controller 14 may increase the trigger volume set by the clinician 16 during periods of the breath where increases in the pressure at the airway of the patient 20 may be induced by changes in the pneumatic system 18, and not by spontaneous efforts of the patient.

Another feature of the ventilator control system is its ability to compensate for gas flow resistance into and out of the lungs of the patient 20. Using the touchscreen 26, the clinician 16 can set a resistance parameter of the patient's respiratory system to a selected value. Alternatively, the display controller 12 may calculate a value for the gas flow resistance from gas flow and pressure measurements provided by the sensor monitoring system 19. The gas flow resistance may be calculated as:

Gas Flow Resistance=(Inspiration Peak Pressure-End Inspiration

Plateau Pressure)/(Inspiration Flow at Peak).

The selected or calculated resistance value is provided to the embedded controller 14 by the display controller 12. The embedded controller 14 adjusts one or more controls of the pneumatic system 18 to compensate for the resistance to flow. The compensation for resistance to flow may be selected to occur during any one or more of the inspiration, exhalation or post-breath phases of a breath. Further, the controls may be adjusted to compensate for different selected or calculated resistance during different phases of a breath.

2. Display Controller—The display controller is an intelligent assistant for the clinician. The display controller quickly informs the clinician of the effects of intervention, provides fast, graphical feedback of his inputs, and presents information in a manner that requires minimal training to understand.

Figure 3:
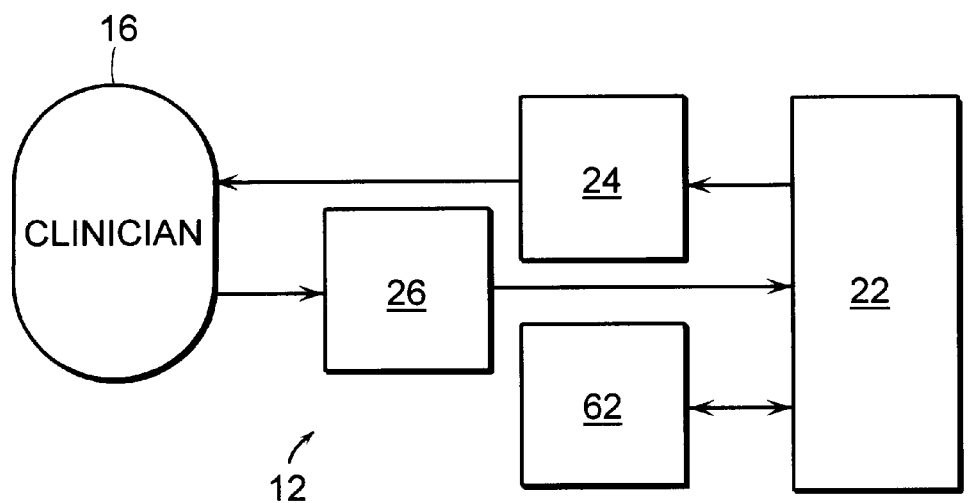
FIG. 3 is a detailed block diagram of a display controller.

Referring to FIG. 3, the display controller 12 is a powerful graphics workstation with hardware and software components. The clinician interacts with the display controller via a color CRT monitor 24 and a resistive touchscreen 26. The monitor has been modified to run from an isolated power supply, and the touchscreen power supply and controller are built in to the monitor. The processor 22 includes a single board computer comprising a microprocessor, RAM, an integrated high speed graphics driver, and integrated dual port memory. The display controller also includes a hard disk drive 62.

Figure 4:
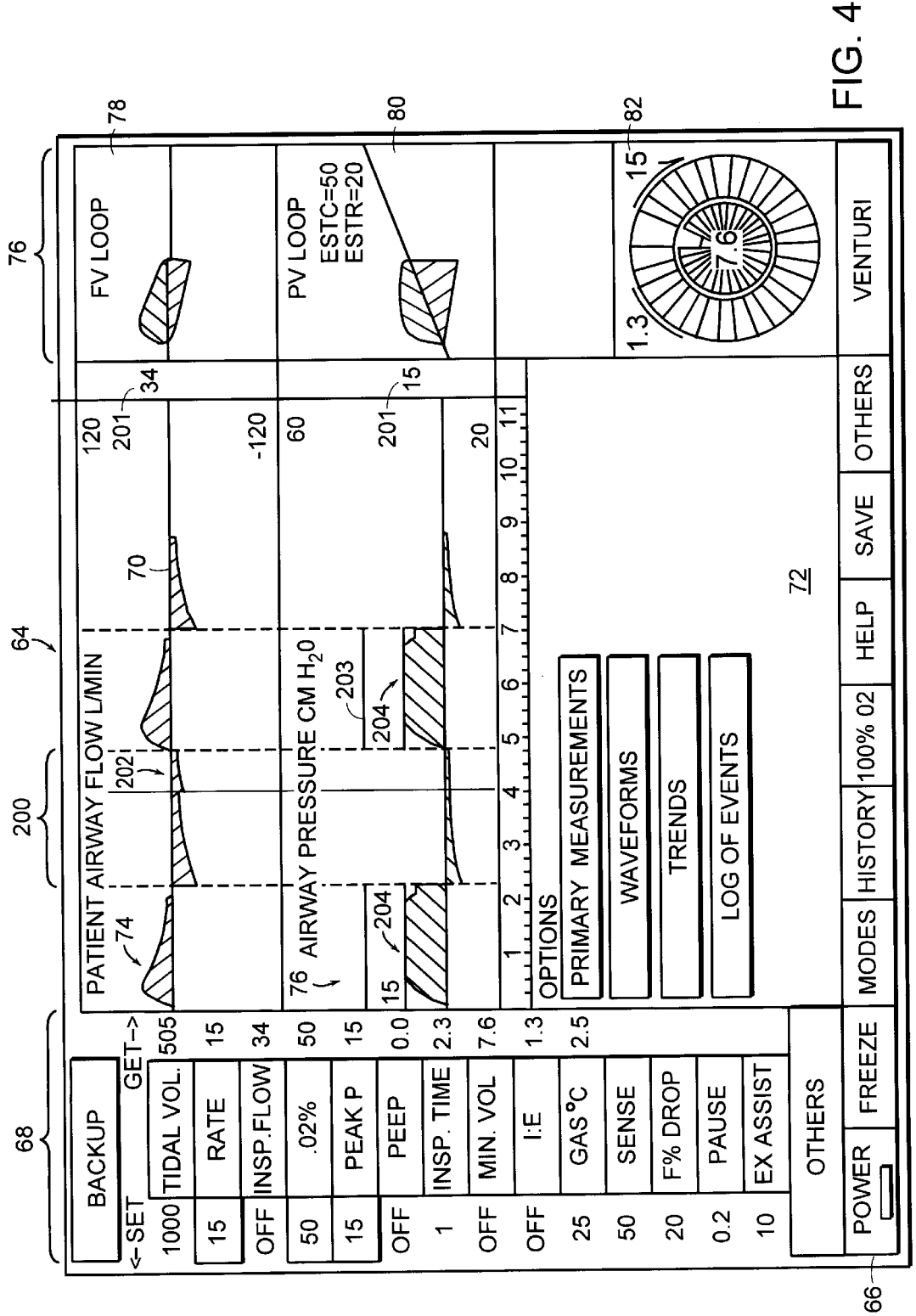
FIG. 4 is an illustration of a display screen when the ventilator control system is in the operational mode.

FIG. 4 is an illustration of a display screen 64 provided by the display controller. The display controller uses software-generated waveforms and software-generated icons for control and alarms settings. The bottom row of on/off buttons 66 includes: a Power button that controls the ventilator control system; a Freeze button to pause the display; a Modes button to display various modes; a History button to play back a database of historical patient protocols; a 100% $O_2$ button to flush the ventilator with oxygen; Help and Save buttons; and an Others button to display other capabilities.

The left side of the screen includes a list of the public ventilator control settings 66. The top area displays the current mode of ventilation (e.g., Backup). Below the top area, each row in the list has three columns. The left column is the current set value. If a row in the left column is inactive, it displays an OFF indication. Important current set values are highlighted. The middle column is a touch sensitive button displaying the abbreviated title of the setting. The right column is the actual value of the setting as measured during the previous breath. If the actual value exceeds an alarm limit, it turns red and a large alarm message is displayed on the screen. By touching a row, a control slider (not shown) appears on the right side of the screen. The control slider enables the clinician to change various parameters (e.g., alarm levels, control settings) and is described in detail below.

The middle area of the display screen is divided into top and bottom regions (70, 72). The bottom region 72 can include a variety of virtual instruments including: additional user-defined waveforms, trendlines, an events log, measured minute averages and other options. The top region 70 includes real time airway flow and pressure waveforms (74, 76), which are displayed over different shades of gray to indicated the breath phase. The airway flow waveform 74 illustrates flow into the patient, or inspiration (positive flow), and flow out of the patient, or exhalation (negative flow). The pressure waveform 76 illustrates that the patient's airway rises above ambient for inspiration and falls during exhalation. The waveforms are tracked by a cursor that can be programmed to follow a peak, average, plateau or manually set position. The waveforms are displayed in fixed axis, moving erase bar format. The time axis resolution is user adjustable and displays time in seconds. Overwriting of the display starts at the beginning of an inspiration, so that the first displayed breath starts at a fixed point on the screen. The vertical axes are scaled to keep the displayed waveforms and settings in clear view.

The right side 76 of the display screen normally includes a flow-volume loop 78, a pressure-volume loop 80 and a minute volume wheel 82. A control slider and other optional panels can overlay this side when a user so desires. The flow-volume loop 78 is updated each breath to show the timing of delivered airflow. The vertical axis of the loop shares a common range and alignment with the airway flow waveform 74. The pressure volume loop is updated each breath to show the condition of the lungs. The vertical axis of the loop shares a common range and alignment with the pressure waveform 76. Calculated resistance and compliance are also displayed.

The minute volume wheel 82 provides a comprehensive summary of the patient's breathing for the last minute. The minute volume wheel displays a wealth of historical breath information (e.g., minute volume, inspiration phase, exhalation phase, inspiration/exhalation ratio, breathing rate, spontaneous minute volume, inhale tidal volume, exhale tidal volume, leakage) on a single integrated graphic circle so that the clinician can readily evaluate ventilation during the last minute.

Figure 5:
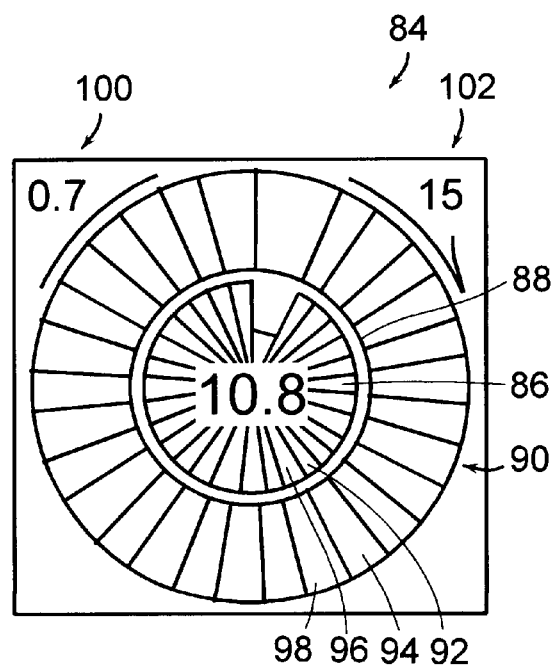
FIG. 5 is an illustration of a section of the display screening showing a minute volume wheel.

Referring to FIG. 5, a minute volume wheel 84 represents one minute of ventilation as a circle with an area corresponding to measured minute volume. The measured minute volume is represented numerically, as the center number, and graphically, as a circle 86 drawn over a background circle 88 that has an area corresponding to the target minute volume. When the measured minute volume is exactly equal to the target minute volume, the two circles are blended in color and appear as one circle. When the measured volume is larger than the target volume, the background circle bleeds through and is visible. When the measured volume is smaller than the target volume, an uncovered portion of the background circle is visible.

One minute of ventilation is drawn as a circle 90, one wedge at a time, and is redrawn once a minute. Like the face of a watch, each degree of the circle 90 corresponds to one sixth of a second. Each inspiration is drawn as a wedge 92 with an area corresponding to delivered volume. This wedge is drawn over an inspiration spoke 94 that extends to maximum minute volume. Each exhalation is drawn as a wedge 96 with an area corresponding to exhaled volume. This wedge is drawn over an exhalation spoke 98 that extends to maximum minute volume. The spokes indicate breathing regularity and inhale to exhale (I:E) time ratio, and the wedges indicate tidal volumes. Difference between the radius of inspiration and exhalation wedges indicates the I:E ratios. The I:E ratio and breathing rate are also represented numerically (100, 102). The pairs of inspiration and exhalation wedges are coded by color to indicate spontaneous breaths, those triggered and partially controlled by the patient, and mandatory breaths, those triggered and controlled by the ventilator. The ratio of the colored areas indicates the ratio of spontaneous to mandatory breathing during the minute just past.

The display controller provides a method for clinician control of the displayed waveforms. Each waveform (74, 76) is continuously measured and displayed on a background that changes color to indicate the phase of a breath. The rectangular area 200 for any phase of the waveform (74, 76) is used as a target for the touchscreen. When the clinician selects a phase of a waveform, the display controller displays the associated ventilator controls for available for adjustment by the clinician.

The display controller provides cursors 201 which are actually floating windows. More specifically, windows of one or two pixels width float over the waveforms (74, 76), thereby creating cursors 201. Since the cursors are independent of the background waveform graphics, numerous advantages result including drawing optimization, dynamic repositioning based on changing waveform values, positioning based on user interface gestures.

The background of the waveform (74, 76) includes color shading to indicate breath phase, title, units and scale information. Redrawing these graphics as new waveform samples are displayed takes too much computer time. Therefore, the display controller performs this function efficiently notwithstanding the complexity of the background image. Background images are created once. A narrow rectangular region 202 is cut from these images and pasted in front of the moving waveform to clear out the previous waveform and refresh the background prior to the new waveform. The width of the rectangular area 202 is kept sufficiently small so that the refresh is smooth in appearance. The x-axis coordinate of the current waveform position is used to control the x-axis position from which to cut out a strip of background image. Multiple color coded background images can be maintained (e.g., three gray shades for the breath phases) and images cut from the desired one depending on the state of the waveform.

Figure 6:
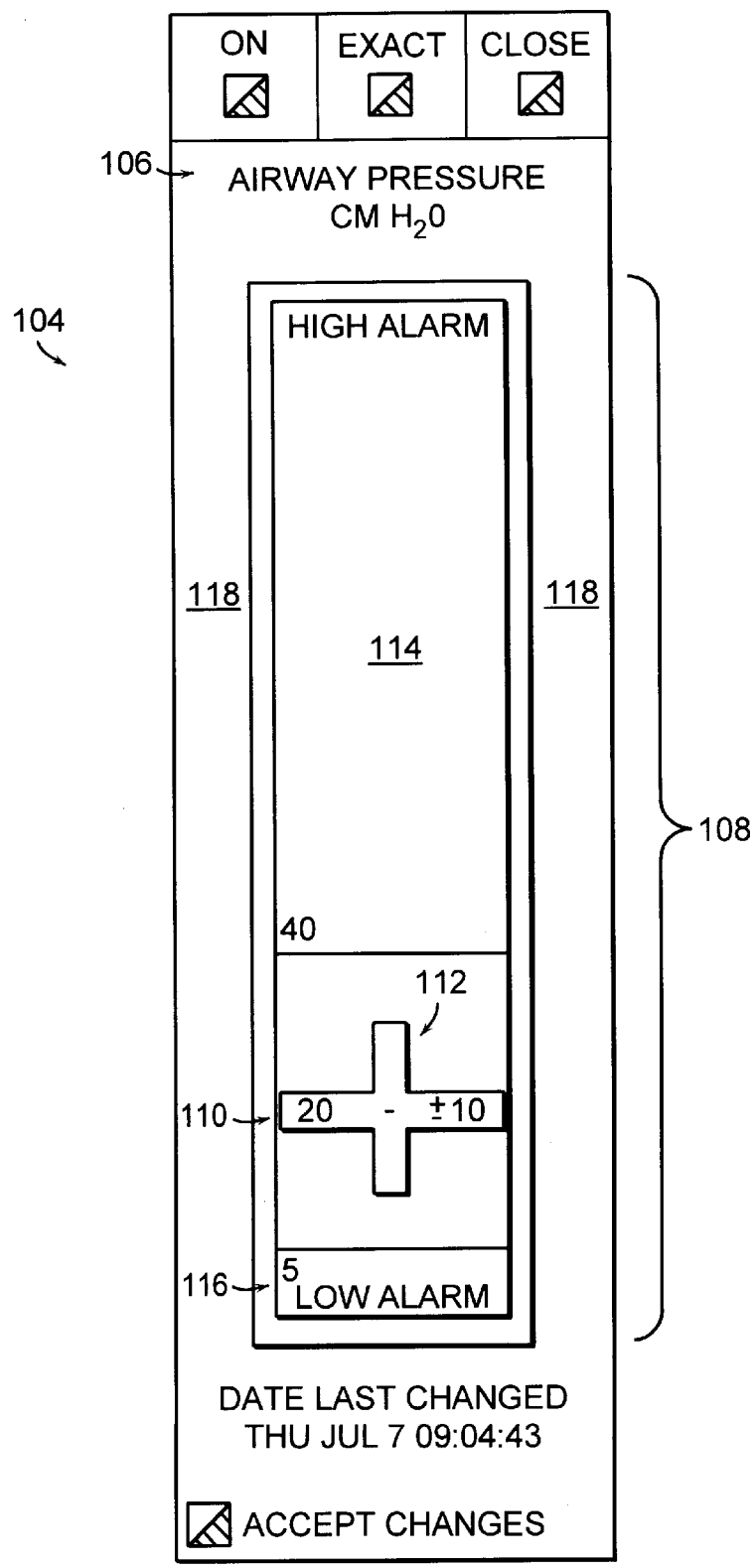
FIG. 6 is an illustration of a section of the display screening showing a control slider.

By selecting a control button, the clinician can display the control slider 106 for the control setting in a fixed location at the right of the screen, as shown in FIG. 6. A scroll bar title 108, located near the top of the slider 106, indicates the name of the control setting. The full vertical range 108 indicates the allowed set limits. The center slider indicates the current position 110 and the range 112 of the control setting. The upper and lower sliders (114, 116) indicate the current alarm limit settings. The position 110 of the current setting within the allowable range 112 and within the alarm limits (114, 116) is readily apparent to the clinician. The clinician can move any of the sliders to change the set values in steps of approximately 1% of the allowable range, or with the "Exact" button selected, approximately ten times more precision (i.e., about 0.1% of the allowable range). When the desired value is reached, the clinician depresses the Accept Changes button to change the parameter.

Alarm settings are matched with control settings in the appropriate control sliders. Some control settings have two associated alarms, others have only one associated alarm or do not have any associated alarms. For example, both high and low inspiratory pressure alarms are provided on the Airway Pressure control slider. If an alarm limit is exceeded during operation, the alarm is displayed in an alarm window, and an audio alarm turns on. Alarms are non-latching, i.e., the alarm indication turns off when the detected level no longer violates the set limit. Available control settings and ranges, alarm settings and ranges, and measured parameters are listed in the following table:

| Control Settings | |
|---|---|
| Tidal Volume (Compliance Compensated) | 50 to 2000 mL |
| Breathing Rate | 2 to 90 bpm |
| Peak Inspiratory Flow (BTPS Compensated) | 10 to 120 LPM |
| Oxygen Percentage | 21 to 100% |
| Peak Inspiratory Pressure | 0 to 120 cm $H_2O$ |
| Exhalation Assist Resistance Compensation | 0 to 60 cm $H_2O$/L/sec |
| PEEP | 0 to 40 cm $H_2O$ |
| Inspiratory Time | 0.2 to 4 sec |
| Inspiratory:Expiratory Ratio | 0.25 to 4.0 |
| Inspiratory Pause Time | 0 to 1 sec |
| Sensitivity (Patient Effort Trigger) | 0 to 250 mL |
| Flow Drop-Off Percentage (Percent of Peak) | 5 to 80% |
| Minute Ventilation - Controlled | 1 to 40 LPM |
| Airway Temperature | 25 to 35 deg C. |
| Waveform Shape | accelerating, decelerating sinusoidal, square |
| Monitored and Displayed Parameters | |
| Exhaled Tidal Volume (Compliance Compensated) | 50 to 2500 mL |
| Measured Breathing Rate | 2 to 150 bpm |
| Peak Inspiratory Flow (BTPS Compensated) | 10 to 200 LPM |
| Oxygen Percentage | 21 to 100% |
| Peak Inspiratory Pressure | 0 to 120 cm $H_2O$ |
| PEEP | 0 to 40 cm $H_2O$ |
| Mean Airway Pressure | 0 to 120 cm $H_2O$ |
| Inspiratory Time | 0.2 to 4 sec |
| Inspiratory:Expiratory Ratio | 0.01 to 99 |
| Minute Ventilation - Controlled | 0 to 99 LPM |
| Minute Ventilation - Spontaneous | 0 to 99 LPM |
| Airway Temperature | 25 to 40 deg C. |
| Lung Compliance | 10 to 150 mL/cm $H_2O$ |
| Airway Resistance | 1 to 60 cm $H_2O$/L/S |
| Leak | 0 to 5 LPM |
| Airway Flow Waveform | −120 to 120 LPM |
| Airway Pressure Waveform | −20 to 60 cm $H_2O$ |
| Flow-Volume Graph, Pressure Volume Graph | see text |
| Fresh Gas Flow Bar Graph | see text |
| Minute Volume Wheel | see text |
| Alarms and Indicators | |
| High/Low Exhaled Tidal Volume Alarm | 0 to 2000 mL |
| High/Low Respiratory Rate Alarm | 2 to 150 bpm |
| Low Oxygen Fresh Gas Flow | Automatic |
| Low Air Fresh Gas Flow | Automatic |
| Low Oxygen Supply Pressure Alarm | 25 psig |
| High/Low Airway Pressure Alarm | 0 to 120 cm $H_2O$ |
| High/Low Inspiratory Time Alarm | 0.2 to 4 sec |
| High/Low Inspiratory:Expiratory Ratio Alarm | 0.05 to 4.0 |
| High/Low Minute Volume Alarm | 1 to 40 LPM |
| Airway Leak Alarm | Leak >25% Fresh Gas Flow |
| Patient Disconnected | |
| Apnea Alarm/Backup Ventilation | 30 sec |
| Internal Battery Notification/Alarm | Battery in Use, Time Remaining |
| Pneumatic System Fault Alarm | |
| Alarms Silence | 120 sec |
| Patient Circuit Alarm | Automatic |
| High/Low Oxygen Alarm | 21–100% Oxygen |

In some embodiments, the display screen is covered by a resistive touchscreen. Known touchscreen interfaces require that the user touch a graphic object on the screen, but this action obscures the object. The touchscreen interface of the present invention defines an area whose shape, size and position is dynamically computed based on the characteristics of the associated graphic object. The interface interprets touching by the user as a manipulation of the associated graphic object. More specifically, a dragging motion moves the associated object, or change its value or other attributes.

Referring to FIG. 6, the display controller includes software for manipulating the characteristics of the breath parameter Airway Pressure displayed in the control slider 104 on the touch-sensitive display. When the clinician selects a control button to display the control slider 106 for Airway Pressure, the display controller dynamically defines a touch zone on the touch-sensitive display. More specifically, touch zones are defined for each slider (i.e., high alarm, low alarm, position and allowable range) within the control slider. Each touch zone is slightly larger than the displayed slider. By way of example only, the touch zone for high alarm may extend into regions 118 to either side of the color coded high alarm region 114. The display controller receives a touch signal when the clinician touches any location within the touch zone and changes the range of the high alarm slider breath parameter in response to the touch signal. In other words, the display controller increases the high alarm limit in response to the clinician touching a location within the region 118 and dragging his finger in a upward path. Because his finger does not obscure the high alarm limit, the clinician can actually see the limit being change as it happens.

Figure 7:
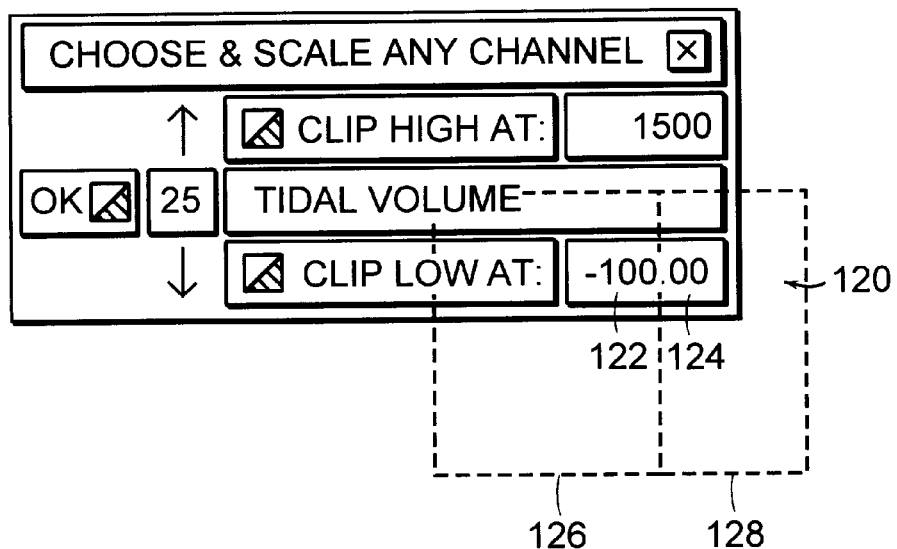
FIG. 7 is an illustration of a section of the display screening showing a numerical controller.

Referring to FIG. 7, the display controller includes software for providing precise numerical control without the requirement of a keyboard. The display controller displays a window 120 that looks like a numeric text field, but has a background color to distinguish the left region 122 from the right region 124, relative to the decimal point. Once either numeric region (122, 124) has been touched, a larger touch sensitive area is associated with each of the numeric regions.

When the clinician touches a touch sensitive area and moves in a vertical path, the interface provides continuous numeric feedback by increasing or decreasing the displayed value.

3. Embedded Controller—The embedded controller electronics is based around a microprocessor 30. The microprocessor provides interfaces to the pneumatic system 18 and the sensors monitoring system 19. The embedded controller relies on industry standard bus based modules to perform certain functions and custom printed circuit boards to perform other functions. The modules, the printed circuit boards and the A/D and D/A module are mounted on or connected to on a main printed circuit board 28. A real time operating system is the foundation of the embedded controller software, which runs the algorithms required for measurement and control. A power system converts line power and provides battery backup for a average of one hour.

The embedded controller has a microprocessor and associated input/output hardware to provide for closed loop control of pneumatic system and the acquisition of patient data. The embedded controller communicates the status of the patient and its own status to the display controller. The embedded controller responds to commands and setting changes received from the display controller, and maintains a non-volatile record of instrument settings to maintain operation in the absence of both communication from the display controller and line power.

The embedded controller performs real time data acquisition of 23 different analog input signals including:
1. Flow . . . Oxygen,
2. Flow . . . Air,
3. Flow . . . Third Gas,
4. Flow . . . Canister,
5. Flow . . . Exhaust,
6. Pressure . . . Patient Airway,
7. Pressure . . . Canister,
8. Flow . . . Low Exhaust,
9. Temperature . . . Airway,
10. Temperature . . . Humidifier,
11. Voltage . . . Battery,
12. Current . . . 5 Volts,
13. $CO_2$ . . . Airway,
14. Voltage . . . ECG,
15. Voltage . . . QRS,
16. Temperature . . . Patient Temperature 2,
17. Pressure . . . Patient Pressure 1,
18. Pressure . . . Patient Pressure 2,
19. Signal . . . PT34,
20. Voltage . . . Aux 1,
21. Voltage . . . Aux 2,
22. Voltage . . . Aux 3,
23. Voltage . . . Aux 4.

The embedded controller also monitors six switches:
1. Pressure . . . Oxygen,
2. Pressure . . . Air,
3. Pressure . . . Third Gas,
4. Pressure . . . Safety Valve,
5. Voltage . . . Power Switch,
6. Voltage . . . No AC Line.

The embedded controller controls nine digital outputs:
1. Solenoid . . . Exhaust Flow Zero,
2. Solenoid . . . Canister Flow Zero,
3. Solenoid . . . Safety Valve,
4. Solenoid . . . Direction (I/E),
5. Heater . . . Canister,
6. Heater . . . Fresh Gas Tube and Humidifier,
7. Power . . . CRT Display,
8. Alarm . . . Beeper,
9. Battery . . . Backup.

The embedded controller controls four duty cycle modulated digital outputs:
1. Flow valve . . . Canister,
2. Flow valve . . . Air,
3. Flow valve . . . Oxygen,
4. Flow valve . . . Third Gas.

The embedded controller 14 communicates with the display controller 12 via a shared memory interface 15 at a data transmission rate exceeding 100K bytes per second.

4. Data Structures—This section describes the architecture for software utilized in the embedded controller and shared with the display controller. The architecture of the software is built around the concepts of therapy controls, mode controls, breath controls, phase controls and cycle controls. A data structure driven state machine determines the control parameters for each therapy control, mode control, breath control, phase control and cycle control.

Figure 10:
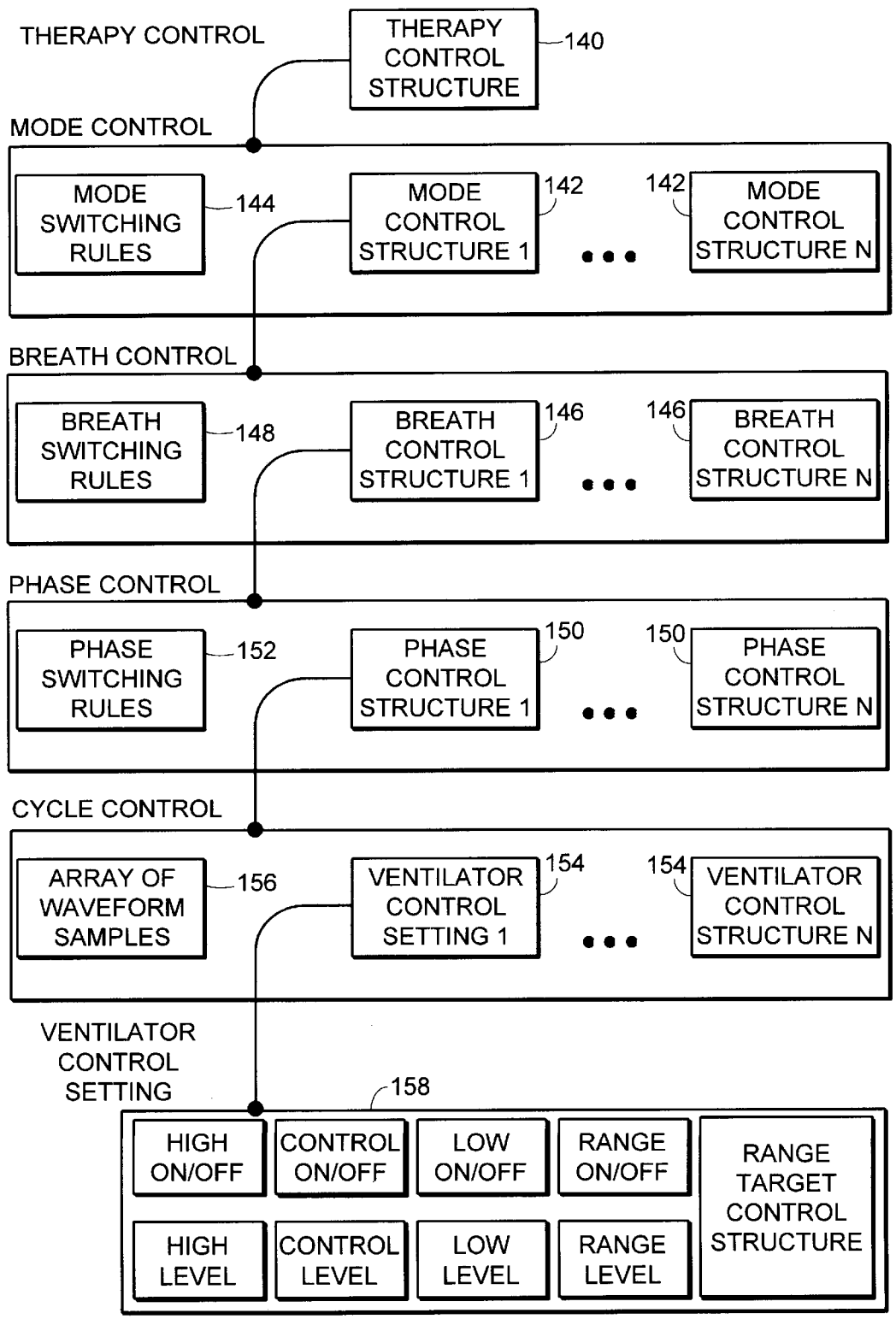
FIG. 10 is a flow chart of the data structure hierarchy employed by the ventilator control system.

FIG. 10 illustrates the data structure hierarchy for the ventilator control system. Using the touch-sensitive display within the display controller, a clinician can change ventilation control settings to create a new therapy comprising a therapy control structure 140. The settings are validated by the display controller, placed into a new therapy control structure and sent to the embedded controller. The embedded controller validates the settings again and checks the integrity of the new structure before the new therapy control is accepted. Also, the clinician may simulate the behavior of the new therapy control using the simulator and may allow others to utilize the therapy control by adding it to the database. In any case, the clinician sends the new therapy control structure to the memory for use by the embedded controller in controller the pneumatic system. A therapy control structure (or a mode control) 140 is defined as a collection of mode control structures 142 and mode switching rules 144. A mode control structure (or a breath control) is defined as a collection of breath control structures 146 and breath switching rules 148. A breath control structure (or a phase control) is defined as a collection of phase control structures 150 and phase switching rules 152. A phase control structure (or a cycle control) is defined as a collection of ventilator control settings 154 and an array of waveform samples 156. Phase definitions and requirements for transitions between phases are tied directly to measurable system performance, and correlate closely to published descriptions of the desired behavior of mechanical ventilators.

More specifically, the therapy control structure 140 is a nested hierarchy of increasingly complex control structures. A cycle (e.g., a 4 msec time slice) occurs within cycle control, which occurs within phase control, which occurs within breath control, which occurs within mode control, which occurs within therapy control, which is the clinically specified therapy that drives the ventilator pneumatic system. Once each cycle, ventilation control moves from one control state to another control state.

After each cycle, when the hierarchy of rules is tested and the state is set for the next cycle, a new therapy control structure 140 may cause a branch to the first cycle of the first phase of the first breath of the first mode of ventilation within the new therapy control structure, or the new therapy control structure may be delayed a few cycles until better patient synchrony can be achieved. Within a therapy, there is a collection of mode control structures 142 and a collection of rules specifying how and when to switch from one mode of ventilation to another one. Thus, a therapy may define several different modes of ventilation and mode switching rules 144 for the transition from one mode of ventilation to another.

After each cycle, when the hierarchy of rules is tested and the state is set for the next cycle, the mode switching rules 144 may cause a branch to the first cycle of the first phase of the first breath of another mode of ventilation within the therapy control structure 140. Within a mode, which is within a therapy, there is a collection of breath control structures 146 and a collection of breath switching rules 148 specifying how and when to switch from one breath type to another breath type within the same mode. Thus, a mode of ventilation may have several different types of breaths defined, and rules specified for how to go from one breath type to another.

After each cycle, when the hierarchy of rules is tested and the state is set for the next cycle, the breath switching rules 148 may cause a branch to the first cycle of the first phase of another type of breath within the mode. Within a breath, within a mode, within a therapy there is a collection of phase control structures 150 and a collection of phase switching rules 152 specifying how and when to switch from one breath phase to another phase within the same breath. Thus, a breath type may have several different phases defined, and rules specified for how to go from one breath phase to another. For example, breathing generally proceeds from an inspiration phase to a pause phase to an exhalation assist phase to a PEEP phase, but these phases may be further subdivided for a finer granularity of control.

After each cycle, when the hierarchy of rules is tested and the state is set for the next cycle, the phase switching rules 152 may cause a branch to the first cycle of the next phase within the breath type. Within a phase, within a breath, within a mode, within a therapy, there is a ventilator control setting structure 154. This structure contains an array of samples that comprise a specified waveform shape. During each cycle, the control logic is driven by the waveform sample specific for the cycle, and by a collection of ventilator control settings 154 specific for the phase. The cycle time is in milliseconds, and is currently set to four milliseconds.

After performing all ventilation control for the cycle, the hierarchy of rules is tested and the state is set for the next cycle, which is by default the next cycle within the current phase, current breath type, current mode of ventilation and current therapy. However, higher level rules may cause a change in breath phase, breath type, mode of ventilation, or an entirely new therapy may be specified by the clinician and take control at the next cycle.

Each ventilator control setting structure 158 contains necessary and sufficient information to control one parameter of ventilation, including whether there is a high alarm level, whether the high alarm is active, whether there is a control level, whether the control is active, whether there is a low alarm level, whether the low alarm is active, whether there is a range level, whether the range is active, and a range target control structure to define how and why the parameter is to be adjusted automatically within the specified range. Each phase control structure has its own collection of ventilator control settings, although in practice, phases within a breath generally share the same collection.

The data structure-driven architecture described above enhances safety and reduces the likelihood of hazardous conditions by permitting non-programmers to review and understand the function of the ventilator control system.

Several breath control structures are predefined in the embedded controller. These breath control structures are used when hazards are detected, such as apnea or patient circuit disconnect. They are also used to support the patient if the communication link between the display controller and embedded controller is lost. Also, the embedded controller checks the integrity of every therapy control structure sent by the display controller. If a requested change is invalid, the embedded controller continues operation with the last known valid therapy control structure. If no valid therapy control structure has been received, the embedded controller uses the predefined breath control structures to continue patient support.

Figure 11:
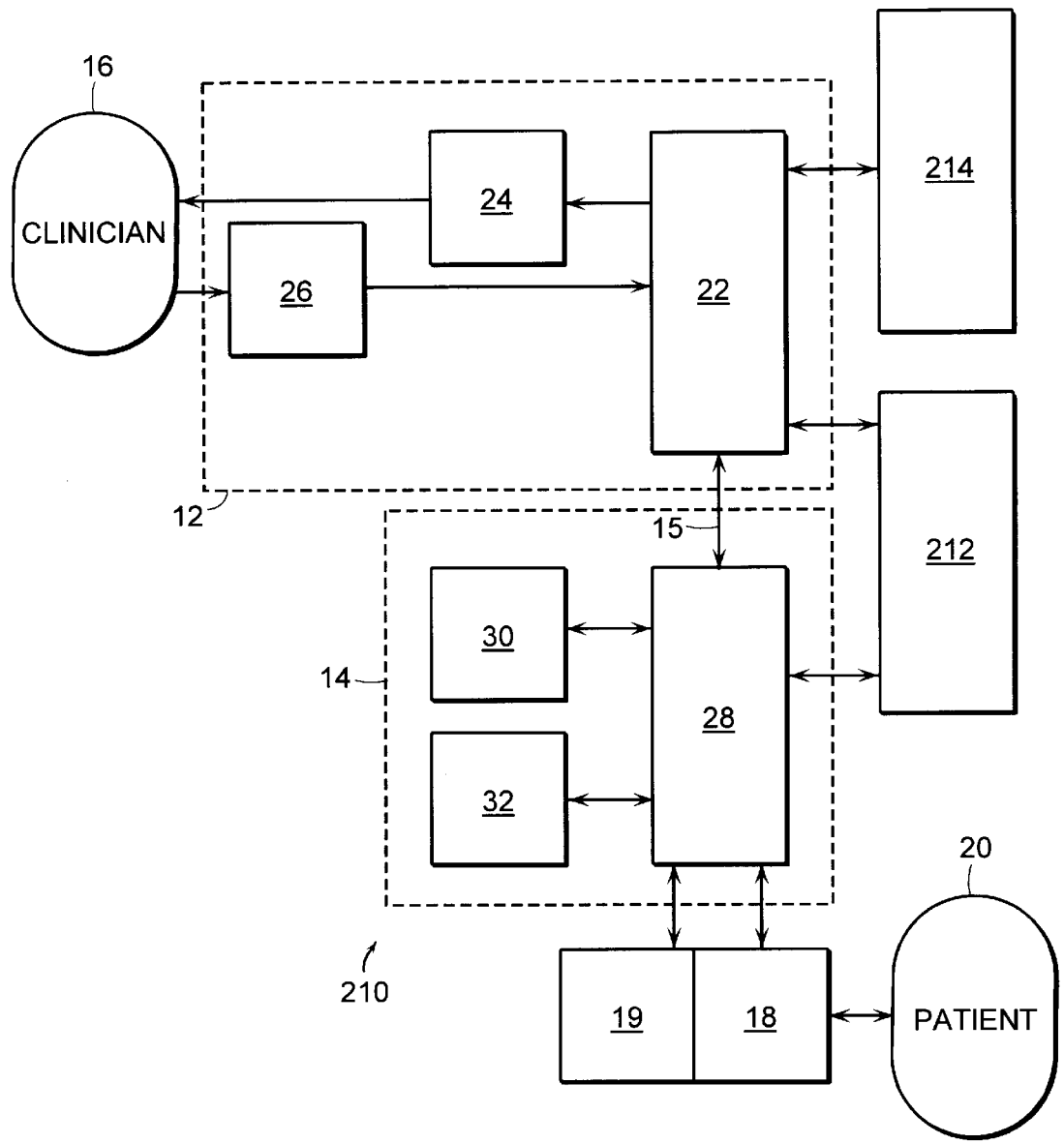
FIG. 11 is a block diagram of a ventilator including a ventilator control system comprising a simulator for predicting the status of the pulmonary system of a patient and a database for storing historical patient protocols.
Figure 12:
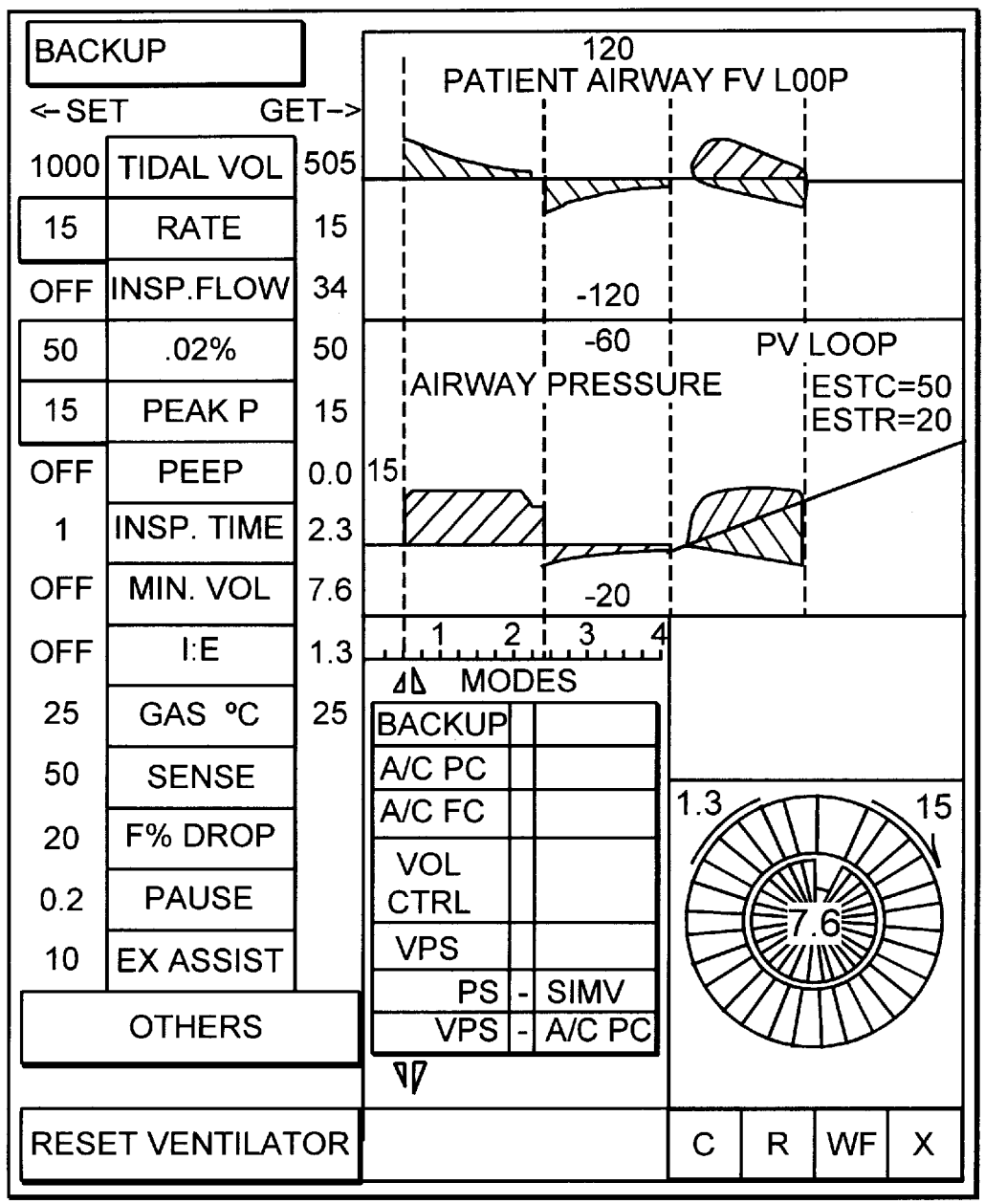
FIG. 12 is an illustration of a simulation mode display screen for the ventilator control system.

5. Simulator—FIG. 11 is a block diagram of a ventilator control system 210 including a simulator 212 for predicting the status of the pulmonary system of a patient and a database 214 for storing actual or simulated historical patient protocols. The simulator 212 is electrically connected to the display and embedded controllers (12, 14). The simulator uses a set of breath parameters provided by the clinician 16 via the touchscreen 26 to predict the status of the patient's pulmonary system. The simulator simulates the adjustment to the ventilator pneumatic system in response to the set of breath parameters and the response of the patient's pulmonary system to the adjusted pneumatic system. The predicted status and the set of breath parameters are displayed on the display screen (FIG. 12).

An advantage of the simulator is that the clinician can experiment with new or old settings, while the actual settings remain unchanged and the patient is unaffected. When the clinician 16 begins changing settings in the simulation mode, the ventilator control system 210 predicts the effects of the change and displays the predicted result on the display 24. The simulator 212 uses a standard two parameter model of a respiratory system and the current calculated values of the patient's resistance and compliance to predict the effect. The model assumes no contribution from the patient's respiratory muscles (i.e., a passive inspiration and exhalation cycle). The model used is:

$$\mathrm{AirwayPressure} = (\mathrm{Delivered\,Volume}/\mathrm{LungCompliance}) +$$
$$(\mathrm{AirwayFlow} \times \mathrm{AirwayResistance}).$$

A change in patient intervention typically requires multiple setting changes. Implementing such setting changes is greatly complicated by the series of indeterminate control states as one setting is changed at a time. Using the simulator 212, the clinician 16 can change multiple settings until the predicted waveforms are satisfactory and then activate all the changes simultaneously. If the clinician is dissatisfied, he can quickly and conveniently return the control settings to their previous values without adversely affecting the patient.

The clinician can also use the simulator 212 to select a mode of ventilation or sequence by modes, by choosing a programmed comprehensive therapy control structure. Those breath parameters, which are essential to the definition of the mode, are highlighted with a color-coded background. Other controls are listed as active or inactive. The explicit list of active controls clearly delineates the exact function of the mode and alleviates confusion caused by inconsistent or incomplete definitions. Moreover, the simulator 212 can precisely replicate the behavior of modes on preexisting ventilators. The clinician can make adjustments to the list of controls to accurately simulate the ventilator that a hospital's staff has been trained to use. The list of controls together with the simulated behavior can help teach the effects of various modes on patients, rather than the ventilator-specific mode definition.

While the simulator 212 shown in FIG. 12 predicts the shape of the breaths using the two parameter model, many other physiological models and predictions may be possible. Specifically, the simulator 212 may predict the effect of positive end expiratory pressure on lung volume and functional residual capacity; it may predict the effect of minute volume on blood oxygen and carbon dioxide levels; it may predict the effect of mean airway pressure on pulmonary blood flow; and it may provide other similar models.

The database 214 assists the clinician in managing the intervention and in tracking patient status. The database makes large amounts of stored patient data available at several levels of detail and encourages comparison of different patient data. The clinician can compare stored historical patient data with current settings to learn whether the current intervention has been effective and whether the patient is progressing.

The database 214 is electrically coupled to the display controller processor 22 and stores a plurality of patient protocols. Each patient protocol includes at least a set of breath parameters and patient data. The breath parameter may be organized as one or more therapy control structures. The clinician selects a patient protocol by depressing a touch zone on the display 24. The processor copies the selected patient protocol into memory. In the operational mode, the processor 22 instructs the embedded controller 14 to simultaneously adjust the controls of the pneumatic system 18 using the selected patient protocol. In the simulation mode, the simulator 212 simulates the adjustment to the ventilator pneumatic system 18 and the resulting response of the patient's pulmonary system.

The processor 22 stores patient protocols as epochs, which are complete "snapshots" of a particular time or event. The processor 22 uses real time event and pattern discrimination to determine when to store epochs of interest. In this way, the clinician does not have to decide a prior what may be important, what to "trend", or how to process the data. Because all the data is stored, it can be post processed to reveal any aspect of the patient's previous condition. The saved epochs are organized in the database. Access to the epochs can be by time, by event, or by area of interest. The ability to overlay data from previous epochs informs the clinician as to whether the patient is progressing, or whether the intervention is working as expected.

Figure 13:
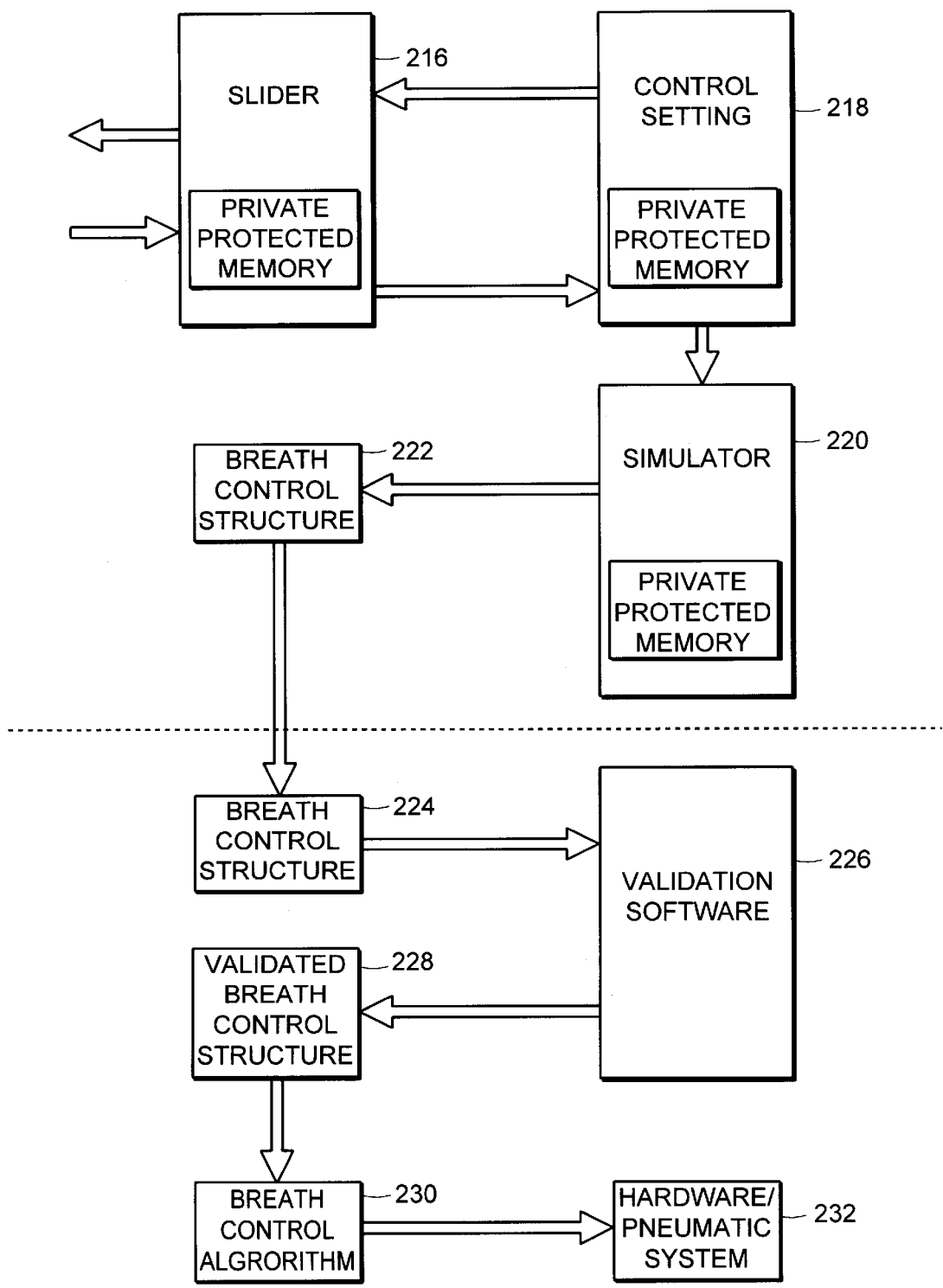
FIG. 13 is a function block diagram of the ventilator control system shown in FIG. 11.

FIG. 13 is a detailed functional block diagram of the simulator feature of the ventilator control system 210. The clinician manipulates a control setting slider 216 to change or set a ventilator control setting. The clinician's input are stored in a memory (at 218). The simulator 220 receives the inputs and creates a phase control structure, a breath control structure, a mode control structure, or a therapy control structure for use in its simulation. If, for example, the clinician decides to use the breath control structure 222 to change the patient's therapy, the breath control structure (which is embedded within a mode control structure within a therapy control structure) is transmitted to the embedded controller (at 224) via the shared memory interface. The real time processor validates the settings within the breath control structure (at 226). The processor implements the validated therapy control structure, which includes the breath control structure 228, in a breath control algorithm 230 and provides signals to the pneumatic system 232 for simultaneously changing one or more control settings.

Figure 8:
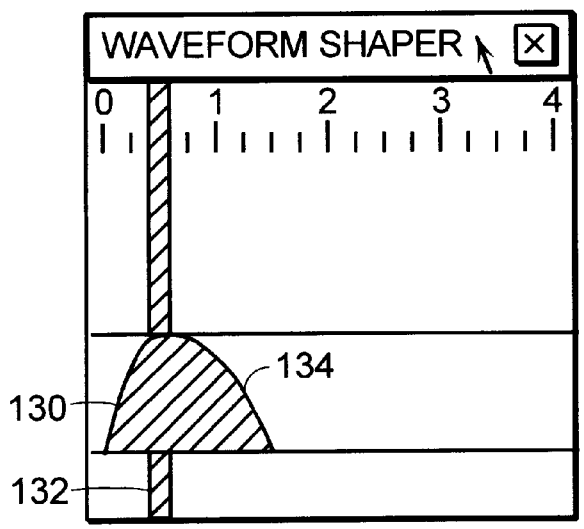
FIG. 8 is an illustration of a section of the display screening showing a waveform shaper.
Figure 9:
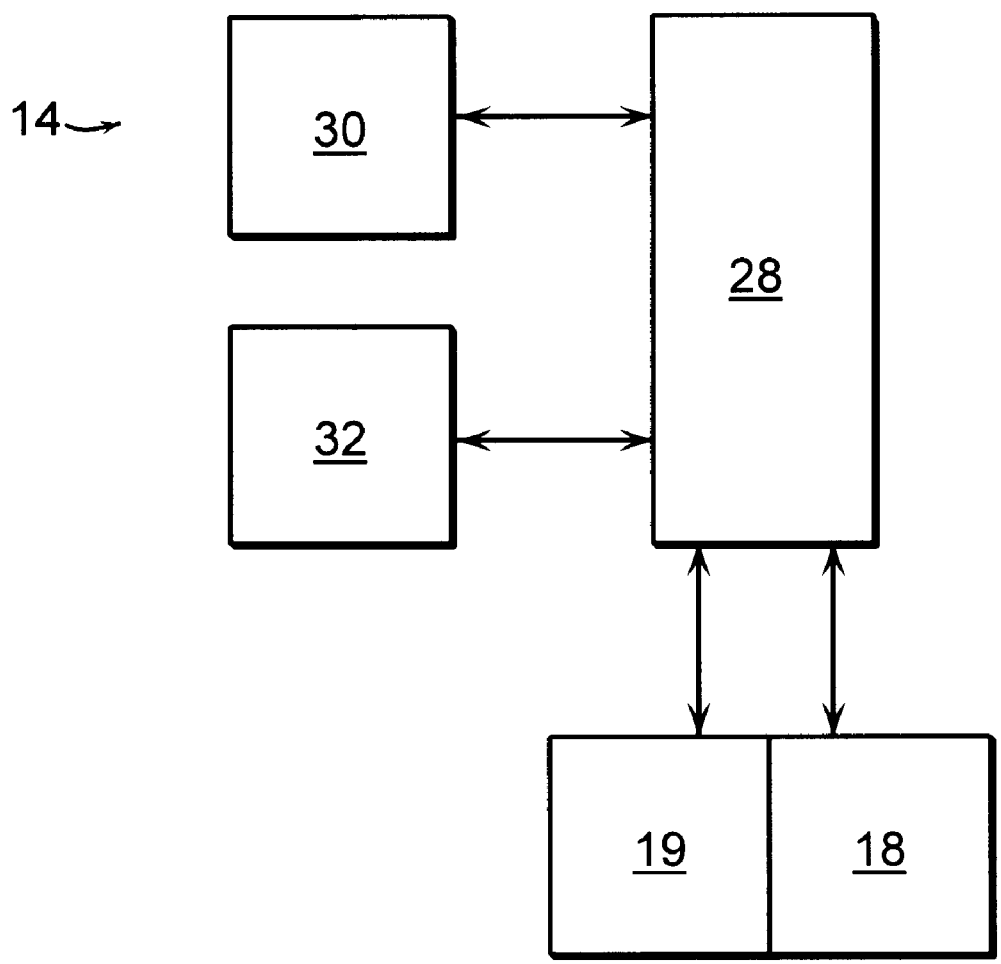
FIG. 9 is a detailed block diagram of an embedded controller.

7. Waveform Shaper—The waveform shaper shown in FIG. 8 is a graphical tool which enables a clinician to shape one or more phases of a breath. Characteristics such as the rise time and shape 130, the plateau length and shape 132, the fall time and shape 134 can be drawn to any desired characteristics by the clinician. In some embodiments, the phases can be shaped by touching the various active areas dynamically created on the waveform shaper and drawing the finger in the desired direction. In other embodiments, control buttons may be selected to add characteristics to the waveform, specifically sinusoidal or pulse-like variations about an average level during a phase. The waveform shaper is electrically connected to the display controller 12, wherein its output is used to fill the array of waveform samples 156 in the cycle control structure of the therapy control structure 140. The pneumatic system 18 connected to the embedded controller 14 can in this way be directed to follow any arbitrary waveform "drawn" by the clinician for one or more phases of a breath.

8. Interface Protocol—The patient data waveforms are driven by a data stream protocol. The data stream can be generated by sensors (the usual way the ventilator operates), by the simulator which uses the breath parameters and measured patient parameters to generate simulated sensor data, or by the stored sensor data in epochs to show historical patient behavior. The ability to use the same interface to display real data, simulated data and epoch data is an important feature of the ventilator control system.

9. Integrated Control/Data/Alarm Display—The patient data waveforms (74,76) presented on display screen 64 of the display controller combine setting control, data and alarm displays in a single region. The association of numbers and graphic icons with the data waveforms provide context to illuminate the meaning of the numbers and icons without unnecessary data or unit labels. A light line at 201 is apparent as peak flow or pressure; a heavy bar at 204 is apparent as the peak pressure set level; a light bar at 204 is apparent as a high pressure alarm setting; an active rectangular region at 200 on the pressure waveform is apparent for setting the exhalation pressure level. Differences between desired and actual settings, and alarm margins are readily apparent. The simplicity of these representations can be contrasted to a typical list of controls, calculated data, and alarms, where each item on the list is in LABEL:VALUE:UNITS format and the integration and comparisons must be performed in the head of the clinician.

Figure 14:
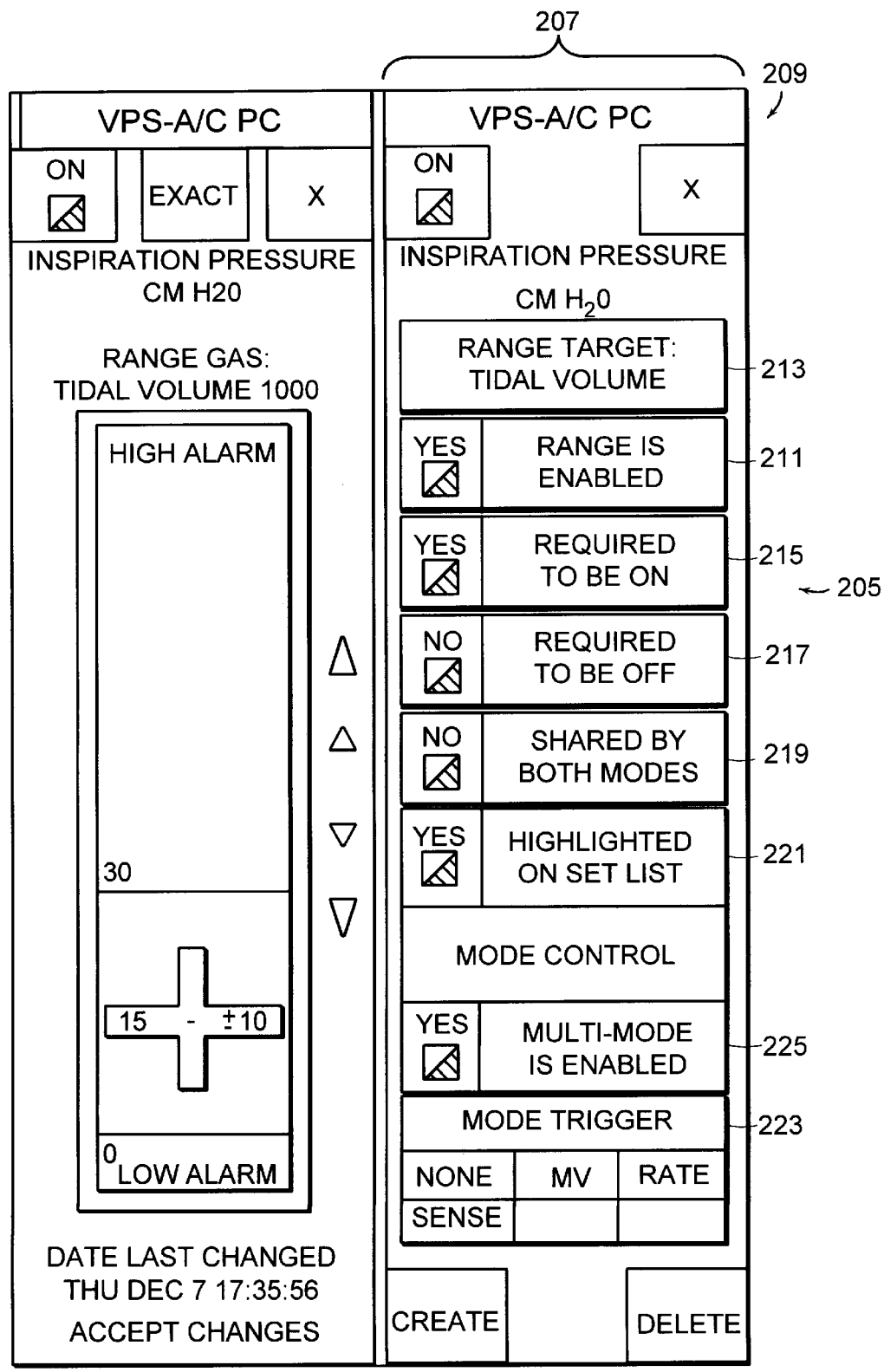
FIG. 14 is an illustration of a therapy programming screen for the ventilator control system.

10. Therapy Programming—FIG. 14 is an illustration of a therapy programming screen 205 provided by the display controller. With this screen, the clinician can create or modify one or many breath parameters to prescribe a new type of therapy for the patient. Changes made are reflected at one or more data structure levels in the therapy control structure created in the display controller. After validation, the new therapy control structure can be sent to the embedded controller for immediate implementation, or saved to a list of therapy prescriptions for later use.

Therapy can thus be built from the simple to the complex. Breath parameters are selected and changed to modify and combine cycles to define a phase; to modify and combine phases to define a breath; to modify and combine breaths to define a mode; and to modify and combine modes to define a therapy program. The selections are reflected in the hierarchy of structures in the therapy control structure, as previously described. The collection of settings are given a title by the clinician, in common use loosely defined as a mode of ventilation. The creation process, with its explicit connection of breath parameters to a mode definition, helps clarify the way the therapy will affect the patient. In contrast, modes preset by the manufacturer often have implicit, obscure and contradictory affects on the patient.

In one embodiment, the therapy programming screen 205 enables selection and changing of related breath parameters.

The therapy prescription to be altered is selected from a list; a new therapy prescription can be created by selecting a similar prescription from the list, giving it a new title, and altering it as needed. A mode within the selected therapy prescription is selected; a breath within the selected mode is selected; a breath parameter control setting within the selected breath is selected; a sequence which identifies a specific, hierarchically nested breath parameter. Features of the breath parameter are toggled on or off, or chosen from lists which are brought forth when there are more than two choices. Every breath parameter, within each breath, within each mode, must be programmed to complete the therapy prescription.

A control definition section 207, is displayed adjacent to the control slider previously described. The control definition section 207 includes a title 209 of the therapy prescription. The title in this example includes two modes, and the mode (A/C pc) to which the selected breath parameter is tied is highlighted. The control setting for the breath parameter may have a range feature enabled 211, which, if enabled, will bring forth a panel of selected targets appropriate for the range, and which, if enabled, means that the ventilator control system will seek to accomplish a range target goal 213 by varying the control setting within the range specified in the control slider. The control setting may be required to be on 215, meaning that it cannot be turned off by the clinician when operating within this breath type within this mode. It may be required to be off 217, meaning that it cannot be turned on by the clinician when operating within this breath type within this mode.

The therapy programming screen allows the control setting to be shared by one or more other breath types 219 within the mode, or within the paired modes, such that any adjustments to the control setting will affect all such breaths. It allows control settings to be highlighted 221 as having primary importance to clinicians making adjustments to therapy. It allows multiple breath types to be defined, and provides a selection of rules that will be tested to determine which breath type to use within the mode.

The embodiment allows the clinician to select from a number of triggers which determine the transition between modes of ventilation 223, when a multimode feature is enabled 225. The triggers for transition may be different depending on the direction of the transition. For the example shown, the trigger for the transition from variable pressure support (VPS) to assist control (A/C pc) is minute volume (MV), while the trigger for the transition from assist control to variable pressure support is sensitivity (Sense, i.e. patient effort).

While the particular embodiment permits the programming of two modes, due to conceptual limitations for this new capability on the part of clinicians, another embodiment includes therapy prescriptions which encompass many modes, with multiple triggers for the transitions between modes. Specifically, other prescriptions include sequences of modes which automatically change the treatment of a patient as his condition changes, and allow the clinician to readily control the sequence. Other prescriptions permit time limited modes, which turn on for a period and then revert to the mode, or combinations of modes, in effect prior to their turn on. The therapy programming screen enables the clinician to tune the therapy to the specific and ever changing needs of the patient, with much more power and flexibility than selecting from a set of simple ventilator modes preset by the manufacturer.

Equivalents

While the invention has been particularly shown and described with reference to specific embodiments, it should be understood by those skilled in the art that various changes in form and detail may be made therein without departing from the spirit and scope of the invention as defined by the appended claims.

We claim:

1. A ventilator control system for controlling a ventilator pneumatic system comprising:

a display controller comprising a processor for creating a breath control structure from a set of breath parameters, and a user interface for receiving input values from a user for setting one or more breath parameters within said set of breath parameters to control respiration of said patient;

a memory electrically coupled to the user interface for storing the set of breath parameters; and an embedded controller fierer comprising a realtime processor for simultaneously adjusting a plurality of controls within a ventilator pneumatic system in response to the set of breath parameters.

2. The ventilator control system of claim 1 wherein each breath parameter comprises at least one of a control setting and an alarm setting.

3. The ventilator control system of claim 1 further comprising a display on which software-generated images representing status of the patient's pulmonary system and the set of breath parameters are displayed.

4. The ventilator control system of claim 3 wherein the user interface comprises a touch-sensitive screen disposed over the display for manipulating one or more breath parameters.

5. The ventilator control system of claim 1 wherein a simulator electrically coupled to the embedded controller and the display controller for simulating the status of a patient's pulmonary system in real time prior to adjusting the plurality of controls within said ventilator pneumatic system.

6. A method for controlling a ventilator pneumatic system comprising:

receiving input values from a display controller wherein the input valves provided by a user for setting one or more breath parameters within a set of breath parameters to control respiration of a patient; and using an embedded controller to simultaneously adjust a plurality of controls within a ventilator pneumatic system connected to said patient in response to the set of breath parameters received from the display controller.

7. The method of claim 6 wherein each breath parameter comprises at least one of a control setting and an alarm setting.

8. The method of claim 6 further comprising creating a breath control structure from the set of breath parameters.

9. The method of claim 8 further comprising simultaneously changing the plurality of controls within the ventilator pneumatic system in response to the breath control structure.

10. The method of claim 6 further comprising displaying software-generated images representing status of the patient's pulmonary system and the set of breath parameters on a display.

11. A ventilator control system for simulating status of a patient connected to a ventilator pneumatic system comprising:

a display controller comprising a user interface for receiving input values from a user to define one or more breath parameters within a set of breath parameters to control respiration of said patient;

a simulator electrically connected to an embedded controller and a display controller comprising a user interface for receiving the set of breath parameters, the simulator predicting the status of a patient's pulmonary system by simulating
- (i) an adjustment by the embedded controller to a plurality of controls within the ventilator pneumatic system in response to the set of breath parameters;
- (ii) a response of the patient's pulmonary system to the adjustment to the plurality of controls within the ventilator pneumatic system; and a display on which software-generated images representing predicted status of the patient's pulmonary system and the set of breath parameters are provided.

12. The ventilator control system of claim 11 wherein each breath parameter comprises at least one of a control setting and an alarm setting.

13. The ventilator control system of claim 11 wherein the user interface comprises a touch-sensitive screen disposed over the display for manipulating one or more breath parameters.

14. A method for simulating status of the pulmonary system of a patient connected to a ventilator pneumatic system comprising:

using a display controller comprising a user interface for setting one or more breath parameters within a set of breath parameters to control respiration of said patient;

predicting the status of the patient's pulmonary system by
- (i) using a simulator electronically connected to an embedded controller for simulating an adjustment to a plurality of controls within the ventilator pneumatic system in response to the set of breath parameters; and
- (ii) simulating a response of the patient's pulmonary system to the adjustment to the plurality of controls within the ventilator pneumatic system; and using a display controller for displaying software-generated images representing the predicted status of the patient's pulmonary system and the set of breath parameters.

15. The method of claim 14 further comprises using an embedded controller to create at least one breath control structure from the set of breath parameters.

16. The method of claim 15 further comprising simulating the adjustment of the plurality of controls within the ventilator pneumatic system in response to the breath control structure.

17. A method for generating a breath control structure to control a ventilator pneumatic system comprising:

providing to a processor a set of breath parameters, each breath parameter within the set of breath parameters including at least one of a control setting or alarm setting;

setting a display controller via a user interface control settings and alarm settings for one or more breath parameters within the set of breath parameters to control respiration of a patient;

creating a breath control structure from the set of breath parameters; and using an embedded controller comprising a real-time processor for simultaneously adjusting a plurality of controls within a ventilator pneumatic system in response to the breath control structure.

18. A method for generating a mode control structure to control a ventilator pneumatic system comprising:

a) providing to an embedded controller a first set of breath parameters, each breath parameter within the first set of breath parameters including at least one of a control or alarm setting;

b) providing user selected input values from a display controller to define the at least one of the control or alarm setting for one or more breath parameters within the first set of breath parameters; and c) creating a first breath control structure from the first set of breath parameters;

d) repeating steps a) to c) for a second set of breath parameters to create a second breath control structure;

e) combining the first and second breath control structures to form a mode control structure; and f) using an embedded controller comprising a real time processor to simultaneously adjust a plurality of controls within a ventilator pneumatic system in response to the mode control structure.

19. A method for providing a therapy to a patient connected to a ventilator pneumatic system comprising:

providing an input via a display controller for a first mode control structure including a plurality of breath control structures to control respiration of said patient and a second mode control structure including a plurality of breath control structures to control respiration of said patient;

using an embedded controller comprising a real-time processor to adjust a plurality of controls within a ventilator pneumatic system using the first mode control structure;

measuring one or more therapy parameters;

employing an embedded controller comprising a real-time processor for simultaneously adjusting the plurality of controls within a ventilator pneumatic system using the second mode control structure when one or more parameters exceed predetermined trigger values.

20. The method of claim 19 wherein a therapy parameter comprises at least one of a time measurement and a characteristic of the patient's pulmonary system.

21. A method for controlling a ventilator pneumatic system comprising:

providing a database to a display controller including a plurality of patient protocols, each patient protocol comprising a set of breath parameters to control respiration of a patient and patient data;

accessing the database to select a patient protocol;

loading a processor with the selected patient protocol, and using an embedded controller comprising a real-time processor to adjust a plurality of controls within the ventilator pneumatic system using the selected patient protocol.

22. The method of claim 21 wherein each breath parameter to control respiration of said patient comprises at least one of a control setting and an alarm setting.

23. The method of claim 21 further comprising predicting the status of the patient's pulmonary system prior to adjusting the plurality of controls by simulating adjusting the plurality of controls within the ventilator pneumatic system in response to the set of breath parameters; and simulating a response of the patient's pulmonary system to the adjustment to the plurality of controls within the ventilator pneumatic system.

24. The method of claim 23 further comprising displaying software-generated images representing the predicted status of the patient's pulmonary system and the set of breath parameters on a display.

25. The method of claim 24 further comprising adjusting the plurality of controls within the ventilator pneumatic system based on the predicted status of the patient's pulmonary system and the set of breath parameters displayed on the display.

26. The method of claim 21 wherein the accessing step further comprises searching the database to select a desired patient protocol.

27. The method of claim 21 further comprising displaying software-generated images representing status of the patient's pulmonary system and the set of breath parameters on a display.

28. A ventilator control system for controlling a ventilator pneumatic system comprising:
   a database which includes a plurality of patient protocols, each patient protocol comprising a set of breath parameters to control respiration of a patient and patient data;
   a display controller comprising a user interface for accessing the database to select a patient protocol; and
   an embedded controller comprising a real-time processor electrically coupled to the user interface for receiving the selected patient protocol, the real-time processor simultaneously adjusting a plurality of controls within the ventilator pneumatic system using the selected patient protocol.

29. The ventilator control system of claim 28 further comprising a display on which software-generated images representing status of the patient's pulmonary system and the set of breath parameters are displayed.

30. The ventilator control system of claim 29 wherein the user interface further comprises a touch-sensitive screen disposed over the display for manipulating one or more breath parameters.

31. A method of compensating for gas flow resistance into and out of the lungs of a patient connected to a ventilator pneumatic system comprising:
   providing a resistance parameter via a display controller;
   measuring the gas flow resistance into and out of the lungs of a patient during an inspiration phase, an exhalation phase and a post-breath phase of a breath; and
   using an embedded controller comprising a real-time processor to selectively adjust one or more controls on the ventilator pneumatic system to compensate for the measured resistance during any one or more of the inspiration, exhalation, or a postbreath phases of the breath to control respiration of said patient.

32. The method of claim 31 further comprising setting the resistance parameter to a selected value.

33. The method of claim 31 further comprising setting the resistance parameter to a selected value using a touchscreen.

34. The method of claim 31 further comprising setting the resistance parameter equal to a value calculated from monitored gas flow and pressure measurements for the patient.

35. A method of displaying historical status of the pulmonary system of a patient connected to a ventilator pneumatic system comprising:
   defining a measurement period of one minute;
   providing to an embedded controller a plurality of breath parameters having user defined target values and actual values, the breath parameters including minute volume, inspiration phase, exhalation phase, inspiration/exhalation ratio, breathing rate, spontaneous minute volume, inhale tidal volume, exhale tidal volume, leakage;
   measuring the actual values during the measurement period;
   generating in a display controller an integrated graphic for displaying the input values and actual values of the plurality of breath parameters on a display, including
      a) representing target minute volume as a circle having an area corresponding to the user defined target value of the minute volume;
      b) representing actual minute volume as a semi-transparent circle disposed over the target minute volume circle and having an area corresponding to the actual value,
      c) representing target inspiration and exhalation phases as interspersed wedges within the target minute volume circle, wherein a target inspiration phase and a target exhalation phase form a target breath, and
      d) representing measured inspiration and exhalation phases as interspersed semi-transparent wedges disposed over the target inspiration and exhalation phase wedges and having an area corresponding to the actual value, wherein a measured inspiration phase and a measured exhalation phase form a measured breath; and
   periodically updating the input values and measured values included in the graphic once per minute.

36. The of claim 35 further comprising representing the inspiration/exhalation ratio and breathing rate as numerical values in the integrated graphic.

37. The method of claim 35 further comprising representing the spontaneous minute volume, inhale tidal volume, exhale tidal volume and leakage as numerical values in the integrated graphic.

38. A method for providing an assisted phase of a breath to a patient connected to a ventilator pneumatic system comprising:
   measuring a flow of gas inhaled by the patient resulting from the patient's spontaneous respiratory muscle activity during an inspiration phase of the patient's respiratory cycle; and
   integrating the measured flow to provide the measured accumulated volume;
   comparing the measured accumulated volume to a trigger volume; and
   adjusting the plurality of controls within the ventilator pneumatic system to control respiration of said patient when the measured accumulated volume exceeds the trigger volume to provide an assisted phase of a breath.

39. A method of compensating for gas flow resistance into and out of the lungs of a patient connected to a ventilator pneumatic system comprising:
   providing a resistance parameter via a display controller;
   setting said resistance parameter equal to a value calculated from monitored gas flow and pressure measurements for the patient, wherein said value is calculated from the following equation;
   resistance parameter=(Inspiration Peak Pressure—End Inspiration Plateau Pressure)/(Inspiration Flow at Peak);
   measuring the gas flow resistance into and out of the lungs of a patient during an inspiration phase, an exhalation phase and a post-breath phase of a breath; and,
   using an embedded controller comprising a real-time processor to selectively adjust one or more controls on the ventilator pneumatic system to compensate for the measured resistance during any one or more of the inspiration, exhalation, or a post-breath phases of the breath.

40. A method of compensating for gas flow resistance into and out of the lungs of a patient connected to a ventilator pneumatic system comprising:

setting the resistance parameter via a display controller equal to a selected value;

measuring the gas flow resistance into and out of the lungs of a patient during a phase of a breath; and using an embedded controller comprising a real-time processor to selectively adjust one or more controls on the ventilator pneumatic system to compensate for the measured resistance during any one or more of the inspiration, exhalation, or a postbreath phases of the breath to control respiration of said patient.

* * * * *

UNITED STATES PATENT AND TRADEMARK OFFICE
CERTIFICATE OF CORRECTION

PATENT NO.    : 5,931,160
DATED         : August 3, 1999
INVENTOR(S)  : Gilmore et al.

It is certified that error appears in the above-identified patent and that said Letters Patent is hereby corrected as shown below:

In col. 22, ln. 16, delete "fierier" and insert --further--;

In col. 22, ln. 21, after "parameter" insert --within a set of breath parameters which define a breath control structure--; and In col. 26, ln 34, after "The" insert --method--.

Signed and Sealed this

First Day of February, 2000

Attest:

Attesting Officer

Q. TODD DICKINSON

*Acting Commissioner of Patents and Trademarks*

(12) EX PARTE REEXAMINATION CERTIFICATE (10465th)
United States Patent
Gilmore et al.

(10) Number: US 5,931,160 C1
(45) Certificate Issued: Jan. 6, 2015

(54) VENTILATOR CONTROL SYSTEM AND METHOD

(75) Inventors: Don Gilmore, Brighton, MA (US); Douglas Johnston, Winchester, MA (US); Gary Schroeder, North Londonderry, NH (US)

(73) Assignee: Ventronics Systems, LLC, Milford, CT (US)

Reexamination Request:
No. 90/012,008, Nov. 15, 2011
No. 90/012,977, Sep. 6, 2013

Reexamination Certificate for:
Patent No.: 5,931,160
Issued: Aug. 3, 1999
Appl. No.: 08/569,919
Filed: Dec. 8, 1995

Certificate of Correction issued Feb. 1, 2000

(51) Int. Cl.
*A61M 16/00* (2006.01)

(52) U.S. Cl.
USPC ............ 128/204.21; 128/204.18; 128/204.23; 128/205.23

(58) Field of Classification Search
USPC ....................................... 128/204.21, 204.23
See application file for complete search history.

(56) References Cited

To view the complete listing of prior art documents cited during the proceedings for Reexamination Control Numbers 90/012,008 and 90/012,977, please refer to the USPTO's public Patent Application Information Retrieval (PAIR) system under the Display References tab.

*Primary Examiner* — Robert M. Fetsuga

(57) ABSTRACT

A ventilator control system controls a ventilator pneumatic system in a medical ventilator. The ventilator control system includes a user interface, a memory and a processor. The user interface receives input values from a user for setting one or more breath parameters within a set of breath parameters. The user interface can include a display for displaying the status of the patient's pulmonary system and the set of breath parameters. The memory stores the set of breath parameters after the user has set one or more breath parameters to desired input values. The processor simultaneously adjusts a plurality of controls within a ventilator pneumatic system in response to the set of breath parameters. The user can change or implement new phases, breaths, modes or therapies in seconds such that the therapy delivered to the patient is essentially uninterrupted. Also, a simulator may be provided for predicting the status of the patient's pulmonary system prior to adjusting the plurality of controls. The predicted status may be displayed adjacent the current status on the display.

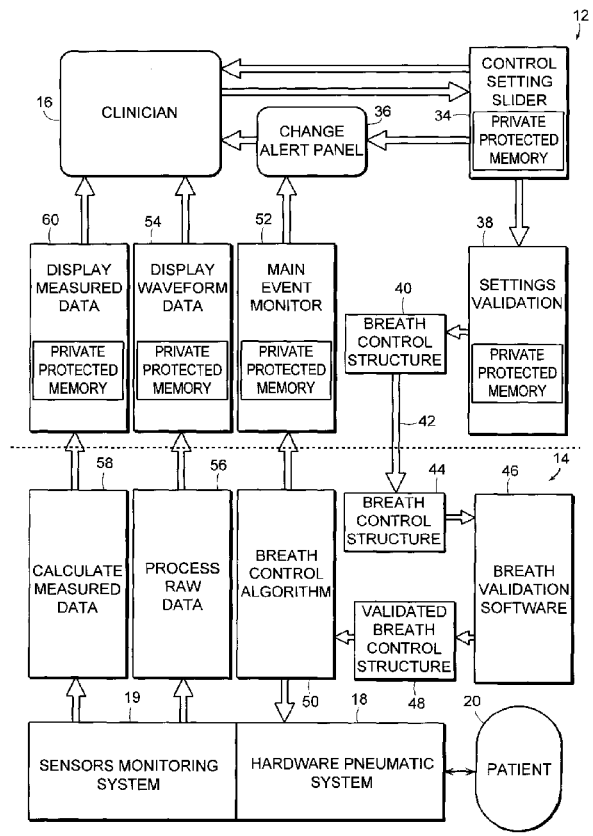

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-4, 6-10, 17, 19-22 and 26-30 are cancelled.

Claims 5, 11-16, 18, 23-25 and 31-40 were not reexamined.

* * * * *